(12) United States Patent
Tsui et al.

(10) Patent No.: US 7,371,525 B2
(45) Date of Patent: May 13, 2008

(54) COMPOSITIONS AND METHODS FOR DIAGNOSING AND TREATING SEVERE ACUTE RESPIRATORY SYNDROME (SARS)

(75) Inventors: Kwok Wing Tsui, Ma On Shan (HK); Siu Chung Stephen Chim, Wan Chai (HK); Mary Miu Yee Waye, Shatin (HK); Kwok Pui Fung, Shatin (HK); Yuk Ming Dennis Lo, Kowloon (HK); Wai Kwun Rossa Chiu, Tai Po (HK); Siu Lun John Tam, Shatin (HK); Kay Sheung Paul Chan, North Point (HK)

(73) Assignee: The Chinese University of Hong Kong, Shatin, N.T. (HK)

( * ) Notice: Subject to any disclaimer, the term of this patent is extended or adjusted under 35 U.S.C. 154(b) by 361 days.

(21) Appl. No.: 10/901,744

(22) Filed: Jul. 28, 2004

(65) Prior Publication Data

US 2005/0095618 A1    May 5, 2005

Related U.S. Application Data

(60) Provisional application No. 60/490,979, filed on Jul. 29, 2003.

(51) Int. Cl.
*C12Q 1/68* (2006.01)
*C12Q 1/00* (2006.01)

(52) U.S. Cl. .................... 435/6; 435/4; 536/23.72; 536/24.32; 536/24.33

(58) Field of Classification Search .................... None
See application file for complete search history.

(56) References Cited

U.S. PATENT DOCUMENTS

2005/0181357 A1*  8/2005  Peiris et al. .................... 435/5

2007/0092938 A1   4/2007  Kwang et al.

OTHER PUBLICATIONS

U.S. Appl. No. 10/948,915, filed Sep. 23, 2004, Lo et al.
U.S. Appl. No. 10/954,815, filed Sep. 29, 2004, Leung et al.
Marra, Marco A. et al.; "The Genome Sequence of the SARS-Associated Coronavirus"; 2003, *Science*, vol. 300, pp. 1399-1404.
Rota, Paul A. et al.; "Characterization of a Novel Coronavirus Associated with Severe Acute Respiratory Syndrome"; 2003, *Science*, vol. 300, pp. 1394-1399.
Ruan, Yijun et al.; "Comparative full-length genome sequence analysis of 14 SARS coronavirus isolates and common mutations associated with putative origins of infection"; 2003, *The Lancet*, vol. 361, pp. 1779-1785.
Tsui, Stephen, K.W. et al.; "Coronavirus Genomic-Sequence Variations and the Epidemiology of the Severe Acute Respiratory Syndrome"; Jul. 10, 2003, *N. Engl. J. Med.* 349;2, pp. 187-188.
Chim, S.S.C. et al.; "Genomic characterization of the severe acute respiratory syndrome coronavirus of Amoy Gardens outbreak in Hong Kong"; Nov. 29, 2003, *The Lancet* vol. 362, pp. 1807-1808.

* cited by examiner

*Primary Examiner*—Bruce R. Campell
*Assistant Examiner*—Louise Humphrey
(74) *Attorney, Agent, or Firm*—Townsend and Townsend and Crew LLP

(57) ABSTRACT

The present invention relates to the fields of immunochemistry and pharmacology. Methods and compositions are described for the diagnosis and treatment of SARS CoV infection. More specifically, the application discloses nucleic acids and peptides of the spike glycoprotein of SARS CoV that provide prognostic and therapeutic compositions in treatment of individuals contracting, or in danger of contracting SARS CoV. The peptides of the invention are also useful in producing antibodies against the SARS CoV glycoprotein.

4 Claims, 8 Drawing Sheets

A. Geographical relationship of Hong Kong and other cities in China

B. Epidemiological analysis of SARS outbreak in China

FIG 7

BLASTX alignment of sequence 1 with the SARS-CoV strain Tor2 spike glycoprotein [SARS coronavirus Tor2]
Length = 1255  Score = 365 bits (937), Expect = e-100 Identities = 183/183 (100%), Positives = 183/183 (100%)
Frame = -2

```
Query: 549
NAQALNTLVKQLSSNFGAISSVLNDILSRLDKVEAEVQIDRLITGRLQSLQTYVTQQLIR 370
NAQALNTLVKQLSSNFGAISSVLNDILSRLDKVEAEVQIDRLITGRLQSLQTYVTQQLIR  Sbjct: 937
NAQALNTLVKQLSSNFGAISSVLNDILSRLDKVEAEVQIDRLITGRLQSLQTYVTQQLIR 996

Query: 369
AAEIRASANLAATKMSECVLGQSKRVDFCGKGYHLMSFPQAAPHGVVFLHVTYVPSQERN 190
AAEIRASANLAATKMSECVLGQSKRVDFCGKGYHLMSFPQAAPHGVVFLHVTYVPSQERN  Sbjct: 997
AAEIRASANLAATKMSECVLGQSKRVDFCGKGYHLMSFPQAAPHGVVFLHVTYVPSQERN 1056

Query: 189
FTTAPAICHEGKAYFPREGVFVFNGTSWFITQRNFFSPQIITDNTFVSGNCDVVIGIIN 10
FTTAPAICHEGKAYFPREGVFVFNGTSWFITQRNFFSPQIITDNTFVSGNCDVVIGIIN  Sbjct: 1057
FTTAPAICHEGKAYFPREGVFVFNGTSWFITQRNFFSPQIITDNTFVSGNCDVVIGIIN 1116

Query: 9
NTV 1
NTVSbjct: 1117
NTV 1119
```

Therefore, this sequence encodes the amino acid residues 937 to 1119 of the spike protein. Note that the total of amino acid residues in the spike protein is 1255.

FIG 8

BLASTX alignment of sequence 2 with the SARS-CoV strain Tor2 spike glycoprotein [SARS coronavirus Tor2]
Length = 1255  Score = 292 bits (748), Expect = 6e-79 Identities = 140/141 (99%), Positives = 140/141 (99%)
Frame = +1

```
Query: 1
PMGTQTHTMIFDNAFNCTFEYISDAFSLDVSEKSGNFKHLREFVFKNKDGFLYVYKGYQP  180
PMGTQTHTMIFDNAFNCTFEYISDAFSLDVSEKSGNFKHLREFVFKNKDGFLYVYKGYQP  Sbjct: 143
PMGTQTHTMIFDNAFNCTFEYISDAFSLDVSEKSGNFKHLREFVFKNKDGFLYVYKGYQP  202

Query: 181
IDVVRDLPSGFNTLKPIFKLPLGINITNFRAILTAFSPAQDTWGTSAAAYFVGYLKPTTF  360
IDVVRDLPSGFNTLKPIFKLPLGINITNFRAILTAFSPAQD  WGTSAAAYFVGYLKPTTF  Sbjct: 203
IDVVRDLPSGFNTLKPIFKLPLGINITNFRAILTAFSPAQDI WGTSAAAYFVGYLKPTTF  262

Query: 361
MLKYDENGTITDAVDCSQNPL  423
MLKYDENGTITDAVDCSQNPL  Sbjct: 263
MLKYDENGTITDAVDCSQNPL  283
```

Therefore, this sequence encodes the amino acid residues 143 to 283 of the spike protein. Note that the total of amino acid residues in the spike protein is 1255.

COMPOSITIONS AND METHODS FOR DIAGNOSING AND TREATING SEVERE ACUTE RESPIRATORY SYNDROME (SARS)

This application claims priority to U.S. provisional patent application No. 60/490,979, filed Jul. 29, 2003, the content of which is incorporated herein in the entirety for all purposes.

FIELD OF THE INVENTION

The present invention relates to the fields of immunochemistry and pharmacology in describing methods and compositions for the diagnosis and treatment of SARS CoV infection.

BACKGROUND OF THE INVENTION

Severe acute respiratory syndrome (SARS) is a recently recognized, highly infectious and life-threatening condition. (Lee N, et al., N. Engl. J. Med. 2003 May 15;348(20):1986-94; Poutanen S M, et al., N. Engl. J. Med. 2003 May 15;348(20):1995-2005; Tsang K W, et al., N. Engl. J. Med. 2003 May 15;348(20):1977-85). The World Health Organization issued a global alert on the condition on Mar. 12, 2003. Numerous cases have since been reported in many parts of the world affecting both health care workers and community citizens. Recent data have provided strong evidence that a novel coronavirus is likely to be an etiological agent for SARS. (Ksiazek T G, et al., N. Engl. J. Med. 2003 May 15; 348(20): 1953-66; Peiris J, et al., Lancet 2003;361: 1319-25; Drosten C, et al., N. Engl. J. Med. 2003 May 15;348(20):1967-76). Thus far, little is known about the biology of this SARS-coronavirus (SARS CoV).

The SARS-CoV genome contains 11 open reading frames coding for a replicase, four major structural proteins: spike, nucleocapsid, envelope and membrane, and several proteins of unknown function. Spike protein is a membrane-bound glycoprotein located on the surface of the virion. This glycoprotein is reported to be important for viral entry and may define host range and tissue tropism (Gallagher T M and Buchmeier M J. (2001) *Virology* 279:371-374; Philips J J et al. (2002) *Virology* 301:109-120). Mutations of the spike glycoprotein gene of other coronaviruses have been correlated with altered pathogenesis and virulence (Bernard S and Laude H. (1995) *J Gen Virol* 76 (Pt 9):2235-2241; Leparc-Goffart I et al. (1997) *Virology* 239:1-10; Phillips J J; and Weiss S R. (2001) *Adv Exp Med Biol* 494:115-119).

SUMMARY OF THE INVENTION

The present invention provides medicaments and methods for treating and preventing SARS CoV infection. Accordingly, the present invention provides an isolated therapeutic nucleic acid comprising a first nucleotide sequence having at least 85%, more preferably at least 90%, most preferably at least 95% and ideally at least 98% sequence identity to at least 15, more preferably at least 18, most preferably at least 23 contiguous nucleotides of SEQ ID NO:1 or 3. Alternatively, the isolated therapeutic nucleic acid may have a first nucleotide sequence having at least 85%, more preferably at least 90%, most preferably at least 95% and ideally at least 98% sequence identity to at least 15, more preferably at least 18, most preferably at least 23 contiguous nucleotides complementary to SEQ ID NO:1 or 3. The first nucleotide sequence also specifically recognizes a target nucleic acid hybridizing to SEQ ID NO:1 or 3 under stringent conditions.

Application of the isolated therapeutic nucleic acid to a eukaryotic cell infected with SARS CoV inhibits SARS expression by at least 30%, more preferably 40%, still more preferably 50%, more advantageously 60%, most advantageously 75%, ideally by at least 80%. In some embodiments, the isolated therapeutic nucleic is an antisense nucleic acid. In other embodiments the isolated therapeutic nucleic acid may be an siRNA or a ribozyme.

Some aspects of the therapeutic nucleic acid include modifications to the base and/or sugar moiety of nucleotides forming the nucleic acid. These modifications may also include modifications to the phosphoribosyl bonds forming the "back bone" of the nucleic acid. Generally, these modifications are designed to improve base-pairing with complementary molecules, or to modify the half-life of the therapeutic nucleic acid. In one aspect, the isolated therapeutic nucleic acid includes at least one modified phosphoribosyl bond. A particularly useful modification is a therapeutic nucleic acid that is a peptide nucleic acid. A preferred embodiment of the isolated therapeutic nucleic acid has a first nucleotide sequence complementary to SEQ ID NO:1 or 3.

Other embodiments of the isolated therapeutic nucleic acid have a second nucleotide sequence complementary to the first nucleotide sequence. In these embodiments the first and second nucleotide sequences form a nucleic acid duplex through base pairing of at least 10, more preferably at least 15, most preferably at least 20 contiguous nucleotides. In some aspects, these duplexed nucleotide sequences are siRNAs. In other aspects, the isolated therapeutic nucleic acid is a ribozyme. In some aspects, the therapeutic nucleic acid may be labeled.

Another nucleic acid embodiment of the present invention is an isolated nucleic acid for identifying, or detecting, the presence of SARS CoV in a sample. This embodiment has a nucleotide sequence having at least 85%, more preferably at least 90%, most preferably at least 95% and ideally at least 98% sequence identity to at least 15, more preferably at least 18, most preferably at least 23 contiguous nucleotides of SEQ ID NO:1 or 3, and specifically recognizing a target nucleic acid hybridizing to SEQ ID NO:1 or 3 under stringent conditions. Preferred aspects of this embodiment may be labeled. Still other aspects may have modified nucleotides, as discussed above. A preferred nucleic acid of the invention is a peptide nucleic acid.

Certain nucleic acid embodiments of the present invention are useful in detecting the target nucleic acid SARS CoV in, for example, a nasal discharge, stool sample, blood sample or any other sample containing viral nucleic acid. These embodiments may further include PCR amplification of the target nucleic acid. In these embodiments, the diagnostic nucleic acid is a probe specific for detecting the target nucleic acid. Some aspects of this embodiment may be labeled.

The invention also includes kits for the detection of SARS CoV in a sample. Kit embodiments include an isolated nucleic acid having at least 85%, more preferably at least 90%, most preferably at least 95% and ideally at least 98% sequence identity to at least 15, more preferably at least 18, most preferably at least 23 contiguous nucleotides of SEQ ID NO:1 or 3, and specifically recognizing a target nucleic acid hybridizing to SEQ ID NO:1 or 3 under stringent conditions; and, instructions for using the isolated nucleic acid to determine the presence of SARS CoV in the sample. Some aspects of these kits contain labeled nucleic acids.

A further embodiment includes a vaccine that having an antigenic molecule having an antigenic amino acid sequence having at least 6, more preferably at least 10, most preferably at least 15 and ideally 20 or more contiguous amino acids homologous to at least 6 contiguous amino acids present in SEQ ID NO:2 or 4; and, a pharmaceutically acceptable excipient. Some aspects of the vaccines optionally include an adjuvant. Other aspects have an antigenic molecule that is a fusion molecule. In still other aspects, vaccines include fusion molecules formed from an antigenically neutral carrier protein.

The invention also provides nucleic acid vaccines. These vaccines include an isolated therapeutic nucleic acid having a first nucleotide sequence having at least 85%, more preferably at least 90%, most preferably at least 95% and ideally at least 98% sequence identity to at least 15, more preferably at least 18, most preferably at least 23 contiguous nucleotides of SEQ ID NO:1 or 3, and specifically recognizing a target nucleic acid hybridizing to SEQ ID NO:1 or 3 under stringent conditions, where application of the isolated therapeutic nucleic acid to a eukaryotic cell infected with SARS CoV inhibits SARS CoV expression in the cell by at least 30%, more preferably 40%, still more preferably 50%, more advantageously 60%, most advantageously 75%, ideally by at least 80%. The vaccine may also contain a pharmaceutically acceptable excipient. In some aspects of this embodiment the first nucleotide sequence is complementary to SEQ ID NO:1 or 3. In still other aspects the vaccine include a second nucleotide sequence complementary to the first nucleotide sequence where the first and second nucleotide sequences form a nucleic acid duplex through base pairing of at least 10, more preferably at least 15, most preferably at least 20 base pairs. In some aspects of the embodiment the therapeutic nucleic acid of the vaccine is in the form of an expression system suitable for expressing the first nucleic acid sequence in a cell infected with SARS CoV. Expressing the nucleic acid inhibits SARS CoV expression by at least 30%, more preferably 40%, still more preferably 50%, more advantageously 60%, most advantageously 75%, ideally by at least 80%. Preferable embodiments comprise expression systems for treating infected mammalian cells.

Another embodiment of the invention is an antibody composition recognizing SARS CoV. This composition includes an antibody that specifically binds a peptide having at least 6 preferably more than 9, ideally more than 12, 15 or 16 contiguous amino acids from one of the peptides selected from SEQ ID NOs:2 and 4. This antibody may optionally be conjugated to a label. Preferably embodiments have antibodies that specifically bind to a protein comprising an amino acid sequence having 50%, preferably 60%, more preferably 65%, advantageously 70% more advantageously 75%, selectively 80%, and ideally 85%, 90%, 95%, 98% or 99% identity to SEQ ID NO:2 or 4 and does not bind to the spike glycoprotein of a non-SARS coronavirus. Antibodies of the present invention are not limited to double-chain antibodies, but also include single-chain antibodies, Fab and $Fab_2$ fragments.

Embodiments of the invention also include methods for detecting the presence of SARS CoV in a sample. These methods are performed by contacting the sample with an antibody specifically recognizing a peptide comprising at least 6 preferably more than 9, ideally more than 12, 15 or 16 contiguous amino acids from one of the peptides selected from SEQ ID NOs:2 and 4, and then determining antibody binding to the peptide. Binding of the antibody to a peptide of the sample indicates the sample includes SARS CoV. In some aspects of the method the antibody is conjugated to a label and the determining step includes detecting the label.

The invention also provides methods for detecting the presence of anti-SARS CoV antibodies in a blood sample. These methods are performed by contacting the blood sample with a peptide comprising at least 6 contiguous amino acids selected from SEQ ID NO:2 or 4; and then detecting anti-SARS CoV antibody specifically binding the peptide. In some aspects the peptide is labeled. In other aspects the peptide is bound to a solid support. Preferably, the anti-SARS CoV antibody is IgG type from a first species, and the detecting step further comprises binding the anti-SARS CoV antibody with an anti-IgG antibody from a second species.

BRIEF DESCRIPTION OF THE DRAWINGS

FIG. 7 provides a BLASTX alignment of sequence 1 (SEQ ID NO:2) with the SARS CoV strain Tor2.

FIG. 8 provides a BLASTX alignment of sequence 2 (SEQ ID NO:4) with the SARS-CoV strain Tor2.

DEFINITIONS

Figure 1:
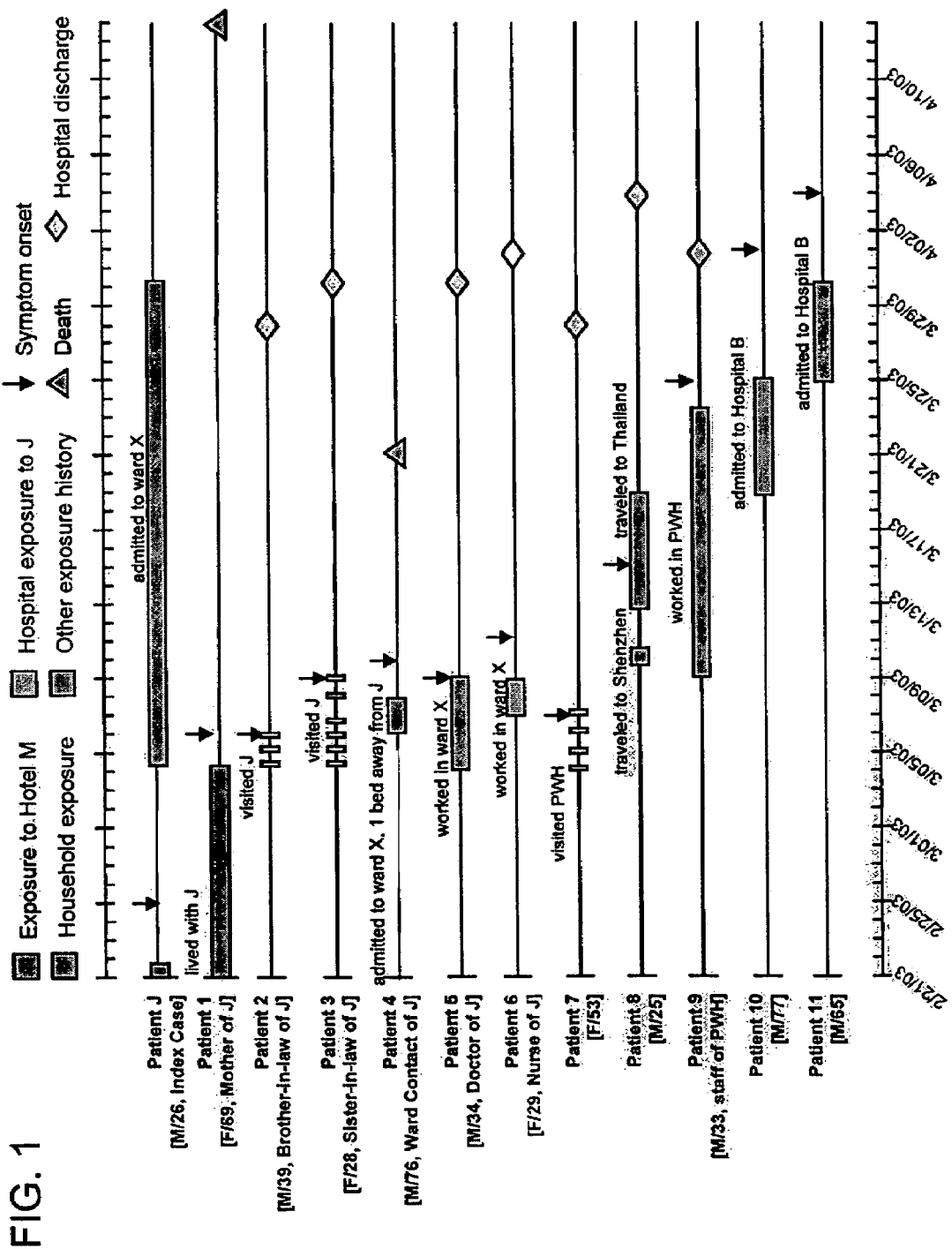
FIG. 1 displays the exposure history and clinical outcome of a cohort of SARS cases in Hong Kong.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology*(2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

The terms "peptide" and "protein" are used herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer. Peptides and proteins of the present invention include amino acid polymers having D- and L-isoforms of individual amino acid residues, as well as other amino acid variants, as described herein. Peptides are distinguished by the number of amino acid residues making up the primary structure of the molecule. For purposes of this invention, peptides are those molecules comprising up to 50 amino acid residues, and proteins comprise 50 or more amino acid residues. However, methods of synthesis and/or delivery of peptides and proteins of the invention are similar, if not identical, as will be appreciated by one of skill in the art. Therefore, where appropriate, these terms are synonymous when discussing methods of synthesis, modification or use as therapeutic or diagnostic reagents.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and o-phosphoserine. "Amino acid analog" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Amino acid sequence" refers to the positional relationship of amino acid residues as they exist in a given polypeptide or protein.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-o-methyl ribonucleotides and peptide-nucleic acids (PNAs).

Unless otherwise indicated, a particular nucleic acid sequence also implicitly encompasses conservatively modified variants thereof (e.g., degenerate codon substitutions, see below) and complementary sequences, as well as the sequence explicitly indicated.

The term "coding sequence," in relation to nucleic acid sequences, refers to a plurality of contiguous sets of three nucleotides, termed codons, each codon corresponding to an amino acid as translated by biochemical factors according to the universal genetic code, the entire sequence coding for an expressed protein, or an antisense strand that inhibits expression of a protein. A "genetic coding sequence" is a coding sequence where the contiguous codons are intermittently interrupted by non-coding intervening sequences, or "introns." During mRNA processing intron sequences are removed, restoring the contiguous codon sequence encoding the protein or anti-sense strand.

"Pharmaceutically acceptable excipient" refers to an inert substance used as a diluent or vehicle for a drug.

"Antibody" or "Functional antibody" refers to a polypeptide ligand substantially encoded by an immunoglobulin gene or immunoglobulin genes, or fragments thereof, which specifically bind and recognize an epitope (e.g., an antigen). Antibodies are structurally defined by the interaction of two forms of polypeptide, one termed an "antibody light chain" and the other termed an "antibody heavy chain". Each antibody light chain is covalently bound to an antibody heavy chain through one or more covalent bonds termed disulfide bridges. Each disulfide bridge consists of a disulfide bond between the γ-sulfide groups of two cysteine residues, one cysteine being part of the antibody heavy chain and the other cysteine being part of the antibody heavy chain. In addition to the covalent association with an antibody light chain, each antibody heavy chain can also be covalently associated with one or more antibody heavy chains. As with the association with antibody heavy and light chains, the interaction between two antibody heavy chains is through one or more disulphide bridges.

Generally, each antibody light chain and each antibody heavy chain is encoded in a separate transcriptional unit, or gene. The present invention however also envisions chimeric antibody genes encoding both heavy and light chains, including, but not limited to, chimeric genes where the coding sequences for heavy and light chains, two heavy chains, or a plurality of any combination of antibody heavy and light chains are joined by a nucleic acid encoding a linker peptide in-frame with the respective antibody-encoding sequences.

The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments discussed below.

The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

Antibodies can exist as intact immunoglobulins or as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to a truncated heavy chain by a disulfide bond. The F(ab)'$_2$ may be reduced under mild conditions to break the disulfide linkage in the hinge region, thereby converting the F(ab)'$_2$ dimer into a Fab' monomer. The Fab' monomer is essentially Fab with part of the hinge region (see *Fundamental Immunology* (Paul ed., 3d ed. 1993)). While various antibody fragments are defined in terms of the digestion of an intact antibody, such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

Generally, a functional antibody is capable of specifically or selectively recognizing one or more epitopes found on an antigen. For example, an "antibody that specifically recognizes a product of the scorable homeostatic reporter element" is an antibody that under designated immunoassay conditions, binds to a protein encoded by a scorable homeostatic reporter element of the present invention with at least two times the background and does not substantially bind in a significant amount to other proteins that might be present in the sample. Typically a functional antibody will bind its antigen in a specific or selective reaction producing a signal at least twice that of the background signal or noise and more typically more than 10 to 100 times background, in a manner that is determinative of the presence of the antigen in a heterogeneous population of antigens and other biologics.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., *Nature* 321:522-525 (1986); Riechmann et al., *Nature* 332:323-329 (1988); and Presta, *Curr. Op. Struct. Biol.* 2:593-596 (1992)). Humanization can be essentially performed following the method of Winter and co-workers (Jones et al., *Nature* 321:522-525 (1986); Riechmann et al., *Nature* 332:323-327 (1988); Verhoeyen et al., *Science* 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

"Antigenic" or "antigen" refers to substances which are capable, under appropriate conditions, of inducing a specific immune response and of reacting with the products of that response, e.g., with specific antibodies or specifically sensitized T-lymphocytes, or both. Antigens may be soluble substances, such as nucleic acids, peptides or proteins, or particulates, such as bacteria and tissue cells; however, only the portion of the protein or polysaccharide molecule known as the antigenic determinant (epitopes) combines with antibody or a specific receptor on a lymphocyte.

"Antigenically neutral carrier protein" refers to proteins that are associated, covalently or noncovalently, with another molecule and do not stimulate an immune response when administered to a host organism.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, 65%, 70%, 75%, 80%, preferably 85%, 90%, 91%, 92%, 93%, 94%, 95%, 96%, 97%, 98%, 99% or higher identity to an amino acid sequence such as SEQ ID NO:2 or a nucleotide sequence such as SEQ ID NO:1 or SEQ ID NO:3), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of HIV envelope glycoproteins, fusion proteins comprising envelope glycoproteins and nucleic acid sequences encoding the same, the BLAST and BLAST 2.0 algorithms and the default parameters discussed below are used.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=-4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=-4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "stringent hybridization conditions" (or "stringent conditions") refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Sequence homology," in the context of amino acid sequences, refers to the correspondence or resemblance of substances belonging to the same type or series; a similarity of composition varying by a small, regular difference, and usually attended by a regular variation in physical properties; as, there is an homology between glycine, alanine, leucine, etc. I.e., the term refers to two sequences differing in homologous amino acid changes in terms of the chemistry of the side groups of corresponding amino acids in the respective sequences.

The terms "complementary" or "complementarity" refer to polynucleotides (i.e., a sequence of nucleotides) related by base-pairing rules. For example, the sequence "5'-AGT-3'," is complementary to the sequence "5'-ACT-3'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance for methods that depend upon binding between nucleic acids.

The phrase "operably linked" refers to a relational orientation of a promoter, terminator and/or control elements to a nucleic acid such that the nucleic acid is operably linked to a promoter, terminator and/or control elements allowing for transcription of the nucleic acid. The promoter, terminator and/or control elements of the construct constitute an "expression system." Expression system may also be used in referring to promoter, terminator and/or control elements operably linked to a nucleic acid encoding a peptide or protein.

A "spike glycoprotein of a non-SARS coronavirus" is any spike glycoprotein of a coronavirus not categorized by the Center for Disease Control as a strain of SARS.

DETAILED DESCRIPTION

I. Introduction

The present invention provides nucleic acids encoding peptides from the SARS CoV spike glycoprotein, and their corresponding amino acid sequences. Methods for using these nucleic acids and peptides in the diagnosis and treatment of SARS CoV are also provided, as are methods for raising antibodies having diagnostic or therapeutic value.

As illustrated in FIG. 1, SARS CoV infection can lead to rapid death. Rapid diagnosis and therapies are therefore a major health concern. FIG. 1 displays the exposure history and clinical outcome of a cohort of SARS cases in Hong Kong. The exposure history, symptom onset and clinical outcome for 12 SARS patients are illustrated. The scale depicts the time course of events that dated before and after the onset of symptoms in each patient. Patients (1 to 7) with documented contact with J and consistent temporal pattern of symptom onset were classified within the secondary infection cohort. Patients 8 to 11 represented cases that were epidemiologically distinct from the secondary infection cohort, in terms of the potential source of exposure and the temporal pattern of symptom onset. Patients 1-9 were admitted to the Prince of Wales Hospital (PWH) which was the hospital with a large outbreak of SARS reported previously (See, Lee N, et al., N. Engl. J. Med. 2003 May 15; 348(20): 1986-94). Patients 8 and 9 did not have direct contact with J prior to symptom onset. Patients 10 and 11 were admitted to Hospital B (20 km away from PWH) and never had direct contact with J or PWH.

Figure 2:
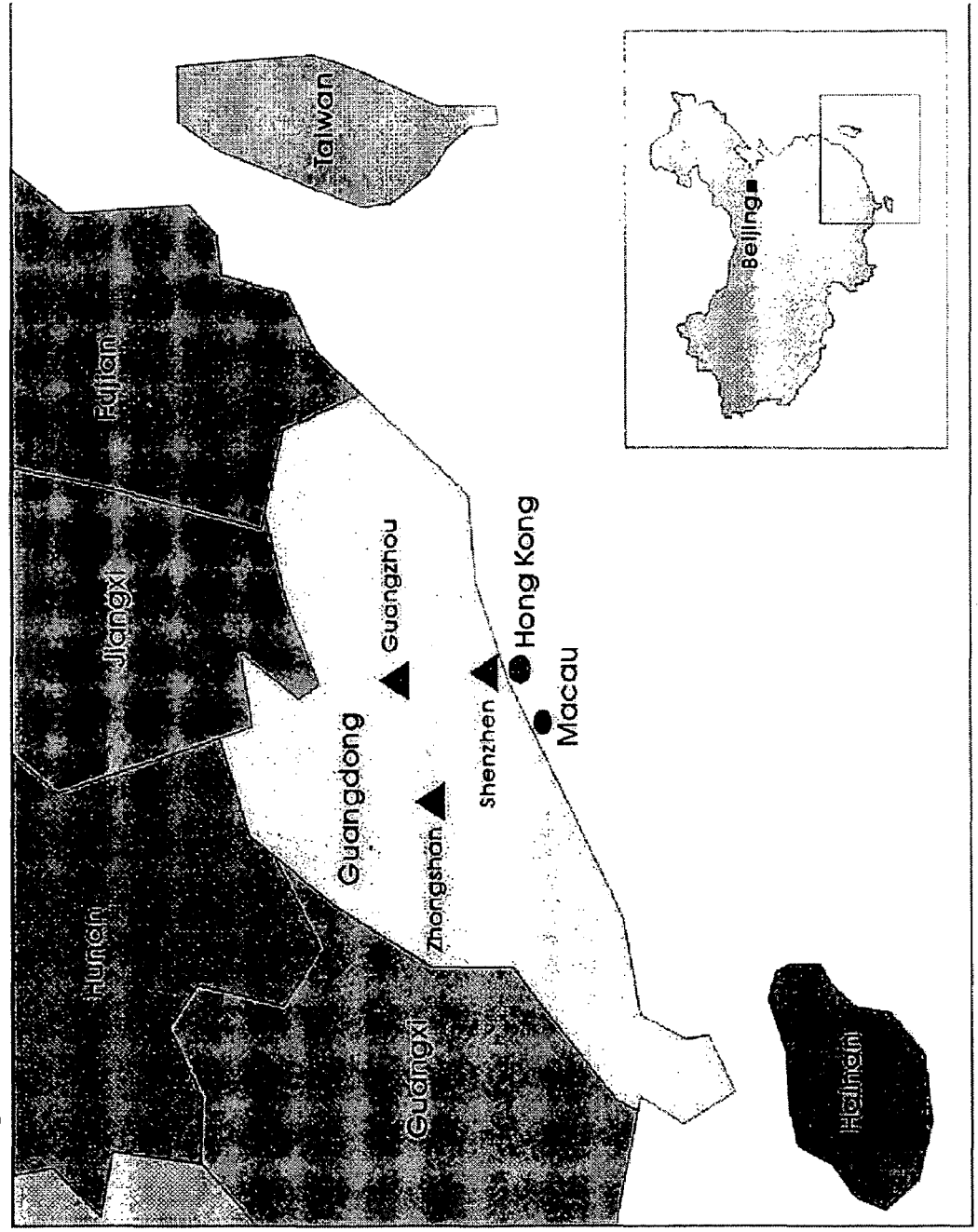
FIG. 2 illustrates the epidemiological relationships of SARS-CoV isolated from cities in China.
Figure 3:
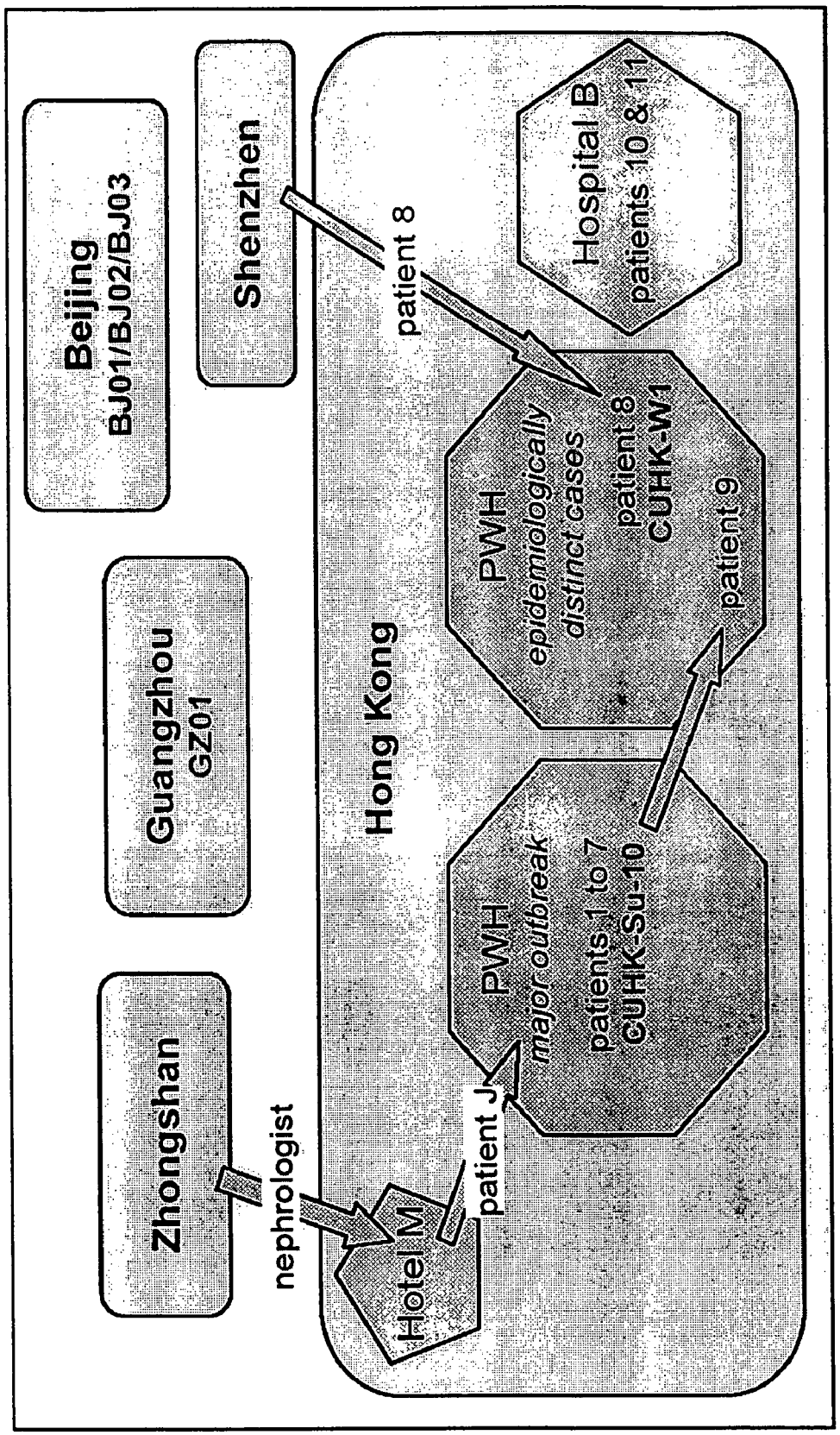
FIG. 3 illustrates the epidemiological relationships of SARS-CoV patients in China.

In modern society, the virus is also capable of spreading rapidly over a wide geographical area. The SARS outbreak in the winter of 2002-2003 included cities in Canada as well as China and south east Asia. Moreover, the virus displays a high mutation rate frequently yielding new, potentially more virulent strains. FIGS. 2 and 3 illustrate the epidemiological relationships of SARS-CoV isolated from cities in China. The geographical relationship of Hong Kong to several Chinese cities is illustrated in panel A. Beijing is located in northern China (see inset) while Zhongshan, Guangzhou and Shenzhen are cities in Guangdong Province, southern China. Zhongshan is located 200 km from the latter two cities, while Guangzhou and Shenzhen are 160 km apart. Hong Kong and Shenzhen are cities that share the same border. The epidemiological relationships of strains of SARS-CoV isolated within China are illustrated in panel B. "PWH" denotes the Prince of Wales Hospital. The epidemiological links between the strains of SARS-CoV isolated are illustrated by arrows. The individuals who were suspected to be involved are also indicated. The names of the strains of SARS CoV isolated from each city or location are indicated below the name of the respective city.

Figure 4:
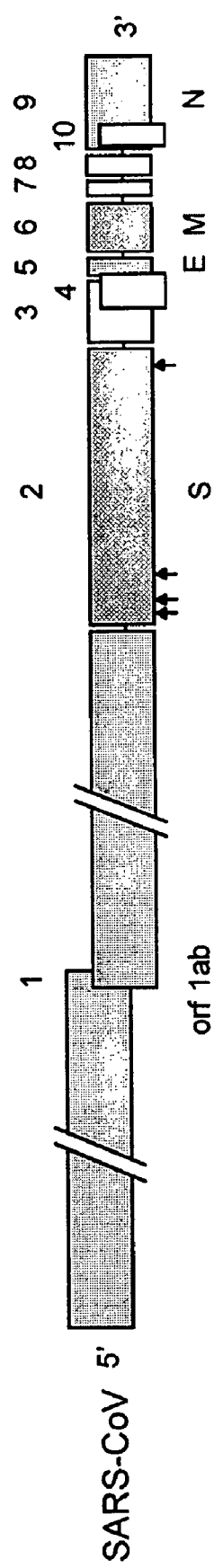
FIG. 4 illustrates the genomic organization of SARS-CoV.

FIG. 4 illustrates the genomic organization of SARS-CoV. The predicted open reading frames (ORFs) of putative proteins and mature peptides of the SARS-CoV are shown according to the annotation conducted by the NCBI (GenBank accession number NC004718). The ORFs are numbered from 1 to 10 and are drawn to scale, except for ORF 1. The size of the complete genome is 29.3 kb, while ORF 1 is 21.4 kb. ORFs showing significant degrees of amino acid homologies corresponding to the predicted orf 1 ab polyprotein, spike glycoprotein, envelope protein, membrane protein and nucleocapsid protein are colored and denoted by orf 1 ab, S, E, M and N, respectively. The viral genome is polyadenylated at the 3' end. The locations of 4 nucleotides subsequently used for spike glycoprotein gene haplotype comparison (see FIG. 4) are indicated by arrows, representing the nucleotide positions, from 5' to 3; 21655, 21721, 22222 and 25114, respectively (numbered according to CDC-Urbani isolate).

Figure 5:
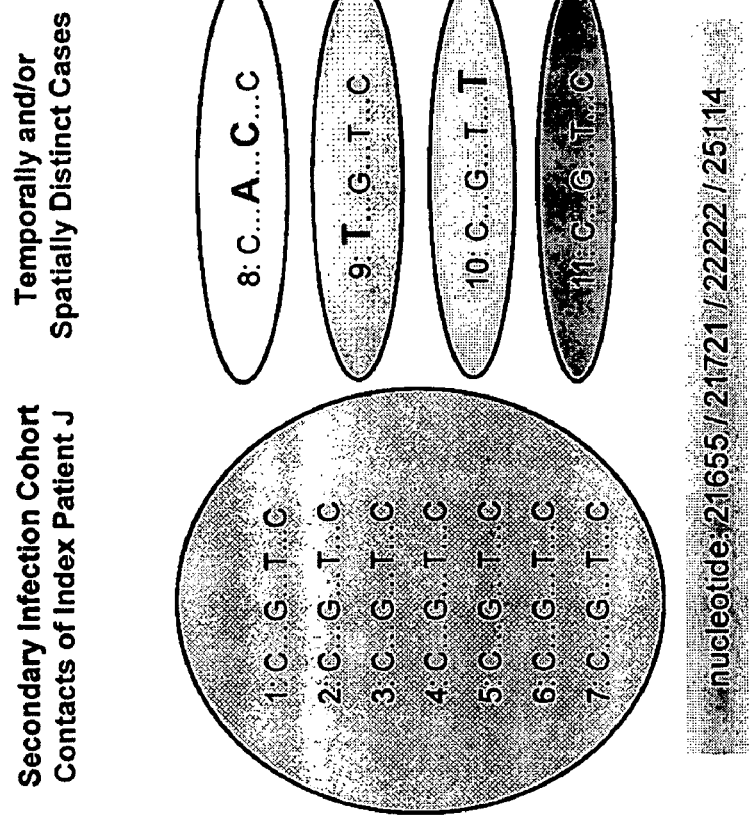
FIG. 5 compares the clinical and molecular epidemiology of SARS Cases in Hong Kong.
Figure 5:
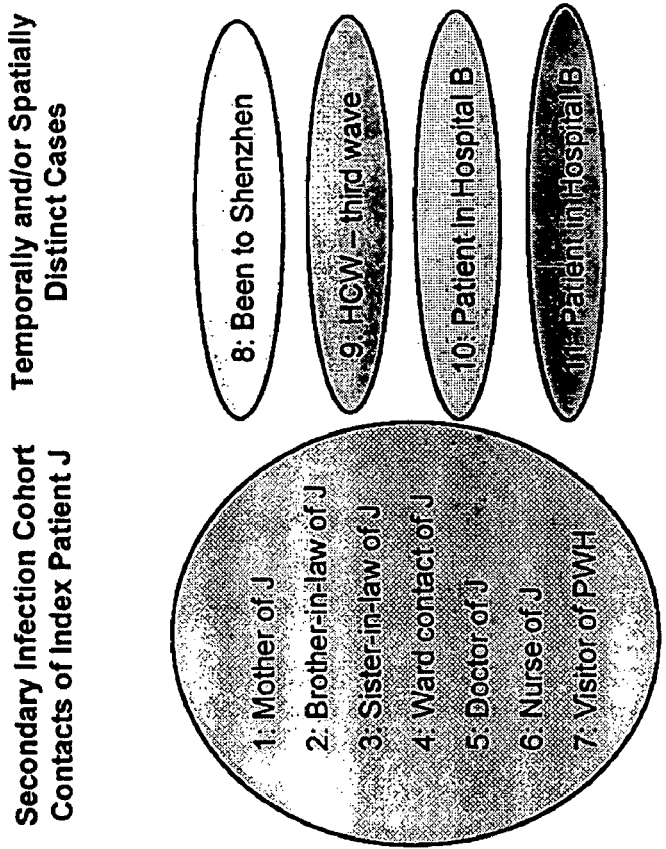

Further illustrating the rapid development of new viral strains, FIG. 5 compares the clinical and molecular epidemiology of SARS Cases in Hong Kong. The clinical epidemiology and spike glycoprotein genotypes of 11 SARS cases are depicted. The exposure history of these cases is illustrated in FIG. 1. Seven cases with history of contact with J and onset of symptoms temporally consistent as secondary infections are included in the cohort (left half of each panel). Four cases with contact history or symptom onset distinct from the secondary infection cohort are also illustrated (right half of each panel). Patients are numbered from 1 to 11. The epidemiological background of each case is briefly described in panel A. Panel B depicts the haplotype comprised of four polymorphic nucleotide positions on the spike glycoprotein gene (as detailed in FIG. 3). Loci of the polymorphic sites are indicated and numbered according to CDC-Urbani isolate. Nucleotide positions with base substitution are depicted in red bold type. PWH: Prince of Wales Hospital; HCW: health care worker.

Figure 6:
FIG. 6 schematically illustrates the relative positions of sequence 1 and sequence 2 in the Spike protein gene of SARS CoV.

All of the nucleic acids and peptides of the present invention are derived from two internal sequences of the SARS CoV glycoprotein, depicted in FIG. 6 schematically as sequence 1 and sequence 2. As shown in FIGS. 7 and 8, BLASTX alignment of these sequences with the SARS CoV strain Tor2 confirms the sequences as being from the spike glycoprotein.

Therapeutic embodiments of the present invention include nucleic acids capable of inhibiting SARS expression in an infected cell. Peptide vaccines for preventing or treating SARS CoV infection are also included. These vaccines are based on antigenic peptides SEQ ID NO:2 or 4, or fragments thereof as provided herein.

Diagnostic embodiments include both reagents and tests for the detection of SARS CoV. The following sections will discuss the construction and use of the nucleic acids and peptides disclosed herein.

II. General Reagents and Methods for Labeling Diagnostic Reagents

Several diagnostic embodiments of the present invention preferably utilize labeled. reagents. This section briefly describes exemplary labels suitable for use with the diagnostic embodiments described herein.

The particular label or detectable group used in the assay is not a critical aspect of the invention, as long as it does not significantly interfere with the specific binding of the nucleic acid or antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination, for example, with antibodies that recognize recombinant SARS CoV Spike glycoprotein domains encompassed within SEQ ID NO:2 or 4, or secondary antibodies that recognize anti-SARS CoV Spike glycoprotein antibodies. Nucleic acid probes and primers, and their targets can be used in similar flexible combinations to provide the most appropriate test for the given application.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorophore with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

III. Nucleic Acids

Nucleic acids of the present invention include both therapeutic and diagnostic reagents. Therapeutic nucleic acids include coding sequences for antigenic peptides, as well as non-coding molecules such as ribozymes, siRNAs and antisense nucleic acids. All therapeutic nucleic acids of the invention are designed to reduce SARS CoV viral load and/or prevent SARS CoV infection of a susceptible individual.

A. Nucleic Acid Synthesis

Nucleic acids of the present invention may be constructed using any suitable method known to one of skill in the art. Basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994).

Nucleic acids may be chemically synthesized according to the solid phase phosphoramidite triester method first described by Beaucage & Caruthers, Tetrahedron Letts., 22:1859-1862 (1981), using an automated synthesizer, as described in Van Devanter et. al., Nucleic Acids Res., 12:6159-6168 (1984). Purification of nucleic acids is by either native acrylamide gel electrophoresis or by anion-exchange HPLC as described in Pearson & Reanier, J. Chrom., 255:137-149 (1983).

Where desirable, one of skill in the art will recognize many ways of generating alterations in a given nucleic acid sequence. Such well-known methods include site-specific mutagenesis, PCR amplification using degenerate nucleic acids, exposure of cells containing the nucleic acid to mutagenic agents or radiation, chemical synthesis of a desired nucleic acid (e.g., in conjunction with ligation and/or cloning to generate large nucleic acids) and other well-known techniques. See, e.g., Berger and Kimmel, Guide to Molecular Cloning Techniques, Methods in Enzymology, Volume 152 Academic Press, Inc., San Diego, Calif. (Berger); Sambrook et al., Molecular Cloning—A Laboratory Manual (2nd ed.) Vol. 1-3, Cold Spring Harbor Laboratory, Cold Spring Harbor Press, N.Y., (Sambrook) (1989); and Current Protocols in Molecular Biology, F. M. Ausubel et al., eds., Current Protocols, a joint venture between Greene Publishing Associates, Inc. and John Wiley & Sons, Inc., (1994 Supplement) (Ausubel); Pirrung et al., U.S. Pat. No. 5,143,854; and Fodor et al., Science, 251:767-77 (1991).

In some embodiments, nucleic acids of the invention may include modified bases as described in Uhlmann, et al. (1990, Chemical Reviews 90: 543-584). Preferred nucleotide analogs are unmodified G, A, T, C and U nucleotides; pyrimidine analogs with lower alkyl, alkynyl or alkenyl groups in the 5 position of the base and purine analogs with similar groups in the 7 or 8 position of the base. Other preferred nucleotide analogs are 5-methylcytosine, 5-methyluracil, diaminopurine, and nucleotides with a 2'—O-methylribose moiety in place of ribose or deoxyribose. As used herein lower alkyl, lower alkynyl and lower alkenyl contain from 1 to 6 carbon atoms and can be straight chain or branched. These groups include methyl, ethyl, propyl, isopropyl, butyl, isobutyl, tertiary butyl, amyl, hexyl and the like. A preferred alkyl group is methyl.

The sequence of isolated nucleic acids may be verified after using, e.g., the chain termination method for sequencing double-stranded templates of Wallace et al., Gene, 16:21-26 (1981) or using the chemical degradation method of Maxam and Gilbert (1980) in Grossman and Moldave (eds.) Academic Press, New York, Methods in Enzymology 65:499-560. Sequences of short oligonucleotides can also be analyzed by laser desorption mass spectroscopy or by fast atom bombardment (McNeal, et al., 1982, J. Am. Chem. Soc. 104: 976; Viari, et al., 1987, Biomed. Enciron. Mass Spectrom. 14: 83; Grotjahn et al., 1982, Nuc. Acid Res. 10: 4671). Analogous sequencing methods are available for RNA.

B. Nucleic Acid Conjugates

Nucleic acids of the invention may include conjugate groups covalently bound to functional groups such as primary or secondary hydroxyl groups. Conjugate groups of the invention include intercalators, reporter molecules, polyamines, polyamides, polyethylene glycols, polyethers, and other groups that enhance the pharmacodynamic properties of oligomers, and groups that enhance the pharmacokinetic properties of oligomers. Typical conjugates groups include cholesterols, lipids, phospholipids, biotin, phenazine, olate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference.

For example, covalent linkage of a cholesterol moiety to a nucleic acid can improve cellular uptake by 5- to 10-fold which in turn improves DNA binding by about 10-fold (Boutorin et al., 1989, FEBS Letters 254: 129-132). Ligands for cellular receptors may also have utility for improving cellular uptake, including, e.g. insulin, transferrin and others. Similarly, derivatization of oligonucleotides with poly-L-lysine can aid nucleic acid uptake by cells (Schell, 1974, Biochem. Biophys. Acta 340: 323, and Lemaitre, et al., 1987, Proc. Natl. Acad. Sci. USA 84: 648).

Certain protein carriers can also facilitate cellular uptake of nucleic acids, including, for example, serum albumin, nuclear proteins possessing signals for transport to the nucleus, and viral or bacterial proteins capable of cell membrane penetration. Accordingly, the present invention contemplates derivatization of the subject oligonucleotides with groups capable of facilitating cellular uptake, including hydrocarbons and non-polar groups, cholesterol, poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes and steroids.

Nucleic acid sizes are given in either kilobases (Kb) or base pairs (bp). These are estimates derived from agarose or acrylamide gel electrophoresis, from sequenced nucleic acids, or from published DNA sequences.

C. Pharmaceutically-Active Nucleic Acids

1. Types of Pharmaceutically-Active Nucleic Acids a) Antisense Nucleic Acids

Antisense nucleic acids provide a means of targeting viral RNA and inhibiting protein synthesis. (See, for example, U.S. Pat. Nos. 5,718,709; 5,610,288; 5,801,154; 5,789,573; 5,739,119 and 5,759,829). Exemplary embodiments of antisense nucleotides include isolated therapeutic nucleic acids including a nucleotide sequence having at least 85% sequence identity to at least 15 contiguous nucleotides complementary to SEQ ID NO:1 or 3, and hybridizing to SEQ ID NO:1 or 3 under stringent conditions. Typical antisense embodiments of the present invention will inhibit SARS CoV expression in an infected cell by at least 30%.

In one embodiment, the antisense nucleic acids comprise DNA or derivatives thereof. In another embodiment, the nucleic acids comprise RNA or derivatives thereof. In a third embodiment, the nucleic acids are modified DNAs, as described previously, preferably DNAs comprising a phosphorothioated modified backbone. In a fourth embodiment, the nucleic acid sequences comprise peptide nucleic acids or derivatives thereof. In each case, preferred compositions comprise a sequence region that is complementary, and more preferably substantially-complementary, and even more preferably, completely complementary to SEQ ID NO:1 or 3. Suitable modifications of antisense nucleic acids are known in the art and discussed in detail herein.

Antisense nucleic acids of the invention may be delivered to cells using any method known to those of skill in the art. In addition to delivery methods discussed below, the use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG peptide coat the antisense nucleic acids and can be delivered into cultured mammalian cells in less than 1 hour with relatively high efficiency (90%). Further, the interaction with MPG strongly increases both the stability of the nucleic acid to nuclease and the ability to cross the plasma membrane.

b) siRNA siRNA molecules are small double-stranded RNAs that elicit a form of sequence-specific gene inactivation. Zamore, Phillip et al., Cell, 101:25-33 (2000). SiRNAs are preferably between 16 and 25, more preferably 17 and 23 and most preferably between 18 and 20 base pairs long, each strand of which has a 3' overhang of 2 or more nucleotides. Functionally, the sequence-specific gene inactivation eli9cited by siRNAs is termed “RNA interference”. RNA interference has been shown to exist in mammalian cell lines, oocytes, early embryos and some cell types (see e.g., Elbashir, Sayda M., et al., Nature, 411:494-497 (2001)). For a review of RNAi and siRNA expression, see Hammond, Scott M et al., Nature Genetics Reviews, 2:110-119; Fire, Andrew, TIG, 15(9):358-363 (1999); Bass, Brenda L., Cell, 101:235-238 (2000).

siRNAs may be introduced to a cell using any means known in the art. Several methods, including gene therapy techniques for introduction of nucleic acids into a cell are detailed below. For example, in addition to transient transfection using siRNA-producing vectors, siRNA molecules may be introduced directly into cells susceptible to, or infected with, SARS CoV. Introducing an siRNA into a cell causes the RNA targeted by the siRNA to be destroyed (Sharp et al., Genes Dev. 13:139, 1999; Wianny et al., Nat. Cell Biol. 2:70, 2000). In certain embodiments of this invention, a control element driving transcription in a SARS CoV-infected cell is operatively linked to a coding sequence for an siRNA targeting SEQ ID NO:1 or 3, or a fragment thereof, of the SARS spike glycoprotein.

c) Ribozymes

The present invention also contemplates therapeutic nucleic acids having nuclease activity, such as ribozymes. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an nucleic acid substrate (Cech et al., 1981; Michel and Westhof, 1990; Reinhold-Hurek and Shub, 1992). This specificity has been attributed to the requirement that the substrate bind via specific base-pairing interactions to the internal guide sequence (“IGS”) of the ribozyme prior to chemical reaction. For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990).

Six basic varieties of naturally-occurring enzymatic RNAs are known presently. Each can catalyze the hydrolysis of RNA phosphodiester bonds in trans (and thus can cleave other RNA molecules) under physiological conditions.

The enzymatic nucleic acid molecule may be formed in a hammerhead, hairpin, a hepatitis δ-virus, group I intron or RNaseP RNA (in association with an RNA guide sequence) or Neurospora VS RNA motif Examples of hammerhead motifs are described by Rossi et al (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359. An example of the hepatitis δ virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071). All of these species are contemplated as part of the present invention, with the substitution of an appropriate nucleotide sequence at the internal guide sequence site. For purposes of the present invention, appropriate nucleotide sequences include any nucleotide sequence having 85%, more preferably at least 90%, most preferably at least 95% and ideally at least 98% identity to a nucleotide sequence complementary to all or a portion of contiguous bases from SEQ ID NO:1 or 3. An aspect of the enzymatic nucleic acid molecules of this invention are that they have a spike glycoprotein recognition site that is complementary to one or more SEQ ID NO:1 or 3 regions, and that it have nucleotide sequences within or surrounding that binding site imparting an RNA cleaving activity to the molecule encoding the spike glycoprotein. Thus the ribozyme constructs need not be limited to specific motifs mentioned herein.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993). In addition, ribozymes of the invention may be delivered to cells using techniques for delivering therapeutic nucleic acids to cells commonly known in the art, preferred methods of which are detailed below.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al., 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

d) Coding Sequences for Antigenic Peptides

While not directly providing inhibition of SARS expression, coding sequences for antigenic peptides are also contemplated as therapeutic nucleic acids of the present invention. Coding sequences for antigenic peptides typically comprise a nucleic acid encoding an antigenic peptide including the amino acid sequence of SEQ ID NO:2 or 4, or fragment thereof. Preferably this nucleic acid is operably linked to an expression system suitable for expressing the nucleic acid in an infected individual. Expression of the coding sequence inhibits SARS CoV in an infected individual by at least 30%.

Antigenic peptides of the present invention are preferably secreted from the cell producing them and induce an immune response against SARS CoV, preferably a $T_H 1$ cellular immune response, in the individual. Accordingly, the coding sequences of the invention have therapeutic use and prophylactic use as vaccine. Antigenic peptides of the invention are discussed in greater detail below.

2. Testing Pharmaceutically-Active Nucleic Acids

Pharmaceutically-active nucleic acids of the invention may be tested using any suitable screening technique known to those of skill in the art. By way of example, inhibition of SARS CoV may be determined in vitro by measuring viral titer produced from cultured cells, e.g., Vero monkey cells. SARS-infected Vero cells may be contacted with a pharmaceutical preparation including varying amounts of therapeutic nucleic acid followed by determination of viral titer. The viral titer from treated cells is compared with the titer produced from untreated cells over the same time period. For purposes of this invention, a putative SARS CoV inhibitor is considered an effective SARS inhibitor if the viral titer from the treated cells is at least 30%, more preferably 40%, still more preferably 50%, more advantageously 60%, most advantageously 75%, ideally by at least 80% less than the viral titer of the untreated cells. Viral titers may be taken, for example, over a course of time or after a fixed elapsed time. Viral titer may be determined using methods known in the art, such as ELISA assay or quantitative RT-PCR. Determination of viral titer provides a direct measure of viral expression, but should not be considered a limitation to the invention as other, equally valid, criteria for determining the effectiveness of viral inhibition may be made. Such alternative criteria include, but are not limited to, cell survival and arrest or inhibition of viral enzyme activity(s). Safe therapeutic levels of pharmaceuticals for human consumption are determined through phase testing using methods well known to those of skill in the art.

3. Administering Pharmaceutically-Active Nucleic Acids

Treatment with nucleic acids of the present invention is preferably transient in nature, although it does not have to be. Ideally, the therapeutic effects persist for the duration of the infection or threat of infection. For therapeutic nucleic acids encoding antigenic peptides, the therapeutic effect is intended to persist not through expression of the nucleic acid, but rather through the "memory" of the host immune system, which persists in an ability to mount an immune response to SARS CoV after both the therapeutic nucleic acid and the peptide or protein it encodes has been cleared from the host.

Pharmaceutically-active nucleic acids are intended for parenteral, topical, oral, local administration or, more preferably, intranasally for prophylactic and/or therapeutic treatment. Generally nucleic acid compositions will be dissolved in a pharmaceutically acceptable excipient, preferably an aqueous excipient. A variety of aqueous excipients may be used, e.g., water, buffered water, 0.4% saline, 0.3% glycine, and the like, including glycoproteins for enhanced stability, such as albumin, lipoprotein, globulin, etc. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of the pharmaceutically-active nucleic acids of the present invention in pharmaceutical preparations can vary widely, i.e., from about 0.001% to as much as 15 or 20% by weight and will be selected primarily by fluid volumes, viscosities, etc., in accordance with the particular mode of administration selected. Actual methods for preparing intranasally, parenterally, orally, and topically administrable compounds will be known or apparent to those skilled in the art and are described in detail in, for example, Remington's Pharmaceutical Science, 17th ed., Mack Publishing Company, Easton, Pa. (1985), which in incorporated herein by reference.

Determination of an effective amount of nucleic to treat hosts afflicted with different ailments may be determined through standard empirical methods well known in the art. For example, immunomodulation may be monitored by serial determinations of leukocyte count, determination of relative and absolute levels of different leukocyte subsets (e.g., CD4$^+$ and CD8$^+$ subsets of T lymphocytes), sedimentation rates, C-reactive protein levels, immunoglobulin levels (particularly those directed at self-antigens), complement levels, and like, as well as general organ function of the host.

In prophylactic applications, nucleic acids of the present invention are administered to a patient susceptible to or otherwise at risk of SARS CoV infection. The precise amount of therapeutically nucleic acid used depends on the patient's state of health and weight. Prophylactic administration may be particularly desirable for individuals that have been exposed or at risk for exposure of infectious diseases, e.g., health-care workers, travelers, family members of infected individuals, immunosuppressed persons, and the like.

As SARS CoV predominantly affects pulmonary tissue, intranasal administration is a preferred method of administering the therapeutic compositions of the present invention. Methods for delivering nucleic acids and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Transmucosal drug delivery in the form of a polytetrafluoroetheylene support matrix is described in U.S. Pat. No. 5,780,045.

Vehicle systems for the delivery of antigens intranasally include polyethylene glycol substituted caprylic/capric acid glycerides and Tween 20™ has been described for use as a mucosal adjuvant (Gizurarson et al., Toxicology 107:61-68 (1996); Gizurarson et al., Vaccine Research 5:69-75 (1996); Gizurarson et al., Vaccine Research 6:41-47 (1997)); however, this formulation produces an uncomfortable stinging sensation in the recipient at the site of administration. Thus, there is a need for an effective formulation for mucosal administration of antigens to produce an acceptable immune response.

4. Formulating of Nucleic Acid Vaccines

Formulation of nucleic acid vaccines is well-known in the art. (Woodrow et al, New Generation Vaccines: The Molecular Approach, Eds., Marcel Dekker, Inc., New York, N.Y. (1989); Cryz, Vaccines and Immunotherapy, Ed., Pergamon Press, New York, N.Y. (1991); and Levine et al, Ped. Ann., 22:719-725 (1993); Tang, D. C., et al. (1992) Nature 356: 152; Fynan, E. F. et al. (1993) PNAS USA 90:11478; Donnelly, J. J. et al. (1995) Nat Med 1:583; Wang, B. et al. (1993) PNAS USA 90:4156; Davis, H. L., et al. (1993) Hum Mol Genet 2:1847; Ulmer, J. B. et al. (1993) Science 259:1745; Robinson, H. L. et al. (1993) Vaccine 11:957; Eisenbraun, M. D. et al. (1993) DNA Cell Biol 12:791; Wang, B. et al. (1994) AIDS Res Hum Retroviruses 10:S35; Coney, L. et al. (1994) Vaccine 12:1545; Sedegah, M. et al. (1994) Proc Natl Acad Sci USA 91:9866; Raz, E. et al. (1994) Proc Natl Acad Sci USA 91:9519; Xiang, Z. Q. et al. (1994) Virology 199:132.

Structurally, therapeutic nucleic acids of the present invention generally include a nucleotide sequence having at least 85% sequence identity to at least 15 contiguous nucleotides of SEQ ID NO:1 or 3, and specifically recognize a target nucleic acid hybridizing to SEQ ID NO:1 or 3 under stringent conditions. Alternatively, therapeutic nucleic acids may include a nucleotide sequence having at least 85% sequence homology to at least 15 contiguous nucleotides complementary to SEQ ID NO:1 or 3, and hybridizing to SEQ ID NO:1 or 3 under stringent conditions.

A new class of vaccines are bacterial vector vaccines is also suitable for use as delivery vehicles for the therapeutic nucleic acids of the invention (See, Curtiss, In: New Generation Vaccines: The Molecular Approach, Ed., Marcel Dekker, Inc., New York, N.Y., pages 161-188 and 269-288 (1989); and Mims et al, In: Medical Microbiology, Eds., Mosby-Year Book Europe Ltd., London (1993)). These vaccines can enter the host, either orally, intranasally or parenterally. Once gaining access to the host, the bacterial vector vaccines express an engineered prokaryotic expression cassette containing the therapeutic nucleic acid operably linked to the expression elements of the cassette. (See, e.g., New Generation Vaccines: The Molecular Approach, supra; Vaccines and Immunotherapy, supra; Hilleman, Dev. Biol. Stand., 82:3-20 (1994); Formal et al, Infect. Immun. 34:746-751 (1981); Gonzalez et al, J. Infect. Dis., 169:927-931 (1994); Stevenson et al, FEMS Lett., 28:317-320 (1985); Aggarwal et al, J. Exp. Med., 172:1083-1090 (1990); Hone et al, Microbial. Path., 5:407-418 (1988); Flynn et al, Mol. Microbiol., 4:2111-2118 (1990); Walker et al, Infect. Immun., 60:4260-4268 (1992); Cardenas et al, Vacc., 11:126-135 (1993); Curtiss et al, Dev. Biol. Stand., 82:23-33 (1994); Simonet et al, Infect. Immun., 62:863-867 (1994); Charbit et al, Vacc., 11:1221-1228 (1993); Turner et al, Infect. Immun., 61:5374-5380 (1993); Schodel et al, Infect. Immun., 62:1669-1676 (1994); Schodel et al, J.

Immunol., 145:4317-4321 (1990); Stabel et al, Infect. Immun., 59:2941-2947 (1991); Brown, J. Infect. Dis., 155: 86-92 (1987); Doggett et al, Infect. Immun., 61:1859-1866 (1993); Brett et al, Immunol., 80:306-312 (1993); Yang et al, J. Immunol., 145:2281-2285 (1990); Gao et al, Infect. Immun., 60:3780-3789 (1992); and Chatfield et al, Bio/Technology, 10:888-892 (1992)).

D. Diagnostic Nucleic Acid Reagents and Methods

The present invention also provides diagnostic nucleic acids for determining the presence and/or severity of a SARS CoV infection. Samples suitable for diagnostic testing can be any tissue or fluid, for example fecal matter, mucosal scrapings, lung, pancreas, small intestine, blood cells, liver, testes, ovaries, colon, skin, stomach, esophagus, spleen, lymph node, bone marrow, kidney or other biological source from the individual suspected of infection with the virus. Other examples include fluid samples such as peripheral blood, lymph fluid, ascites, serous fluid, pleural effusion, sputum, cerebrospinal fluid, lacrimal fluid, and urine.

Diagnostic nucleic acids of the invention may also be useful in determining the particular strain of SARS CoV causing an infection and may therefore also be instruments for tracking the course of infection or identifying new strains of the virus as they appear. For example, using the methods described herein, the nucleotides of the present invention would allow one of skill in the art to distinguish SARS CoV strains having variant spike glycoproteins, as noted in table 1.

In one embodiment, the invention provides an isolated nucleic acid for identifying the presence of SARS CoV in a sample that has a nucleotide sequence having at least 85% sequence identity to at least 15 contiguous nucleotides complementary to SEQ ID NO:1 or 3, and hybridizing to SEQ ID NO:1 or 3 under stringent conditions.

Diagnostic methods include a method for detecting SARS CoV in a sample comprising contacting the sample with a diagnostic nucleic acid having a nucleotide sequence having at least 85% sequence identity to at least 15 contiguous nucleotides of SEQ ID NO:1 or 3, and specifically recognizing a target nucleic acid hybridizing to SEQ ID NO:1 or 3 under stringent conditions. The following sections discuss these reagents and methods in greater detail, providing numerous examples of both reagent and method embodiments of the invention.

1. Genetic Diagnosis

One embodiment of the instant invention comprises a method for detecting SARS CoV infection by determining an increase in the expression of spike glycoprotein by looking at the spike glycoprotein transcripts or the copy number of the spike glycoprotein gene. Another embodiment of the instant invention comprises a method for detecting reduction in SARS CoV titer by examining the spike glycoprotein gene or transcripts. The nucleic acid used is isolated from SARS CoV-infected cells according to standard methodologies (Sambrook et al., 1989). The nucleic acid may be genomic DNA, serum RNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified according to standard procedures.

Spike glycoprotein nucleic acid is identified in the sample directly using amplification with a second nucleic acid having at least 85%, preferably at least 90%, more preferably at least 95% sequence identity to at least 15 contiguous nucleotides complementary to SEQ ID NO:1 or 3, and hybridizing to SEQ ID NO:1 or 3 under stringent conditions. Ideally, the second nucleic acid is identical to SEQ ID NO:1 or 3, or a fragment thereof. The amplification product is detected, optionally after purification, using methods known in the art. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994). Useful labels for diagnostic reagents of the invention are discussed below.

Following detection, one may compare the results seen in a given patient with a control reaction or a statistically significant reference group of normal patients. In this way, it is possible to correlate, for example, viral titer with the severity of infection.

Methods for detection of SARS CoV discussed above are also useful in examining deletions, insertions, and other mutations of SARS CoV that define particular viral strains or are important to virility. Using these techniques, those of skill may track the pattern of infection of particular strains and detect new strains of virus as they emerge. A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific nucleic acid (ASO), dot blot analysis, denaturing gradient gel electrophoresis, RFLP and PCR-SSCP.

Ribozymes may be used as diagnostic tools to examine viral mutations and assess levels of SARS CoV RNA. The close relationship between ribozyme activity and the structure of the target spike glycoprotein allows the detection of mutations in the regions of the molecule corresponding to SEQ ID NO:1 or 3 that alter the base-pairing and three-dimensional structure of the spike glycoprotein RNA. By using multiple ribozymes, one may map nucleotide changes in these sequence regions that are important to RNA structure and function.

2. PCR and Blotting Techniques

Both polymerase chain reaction (PCR) and blotting techniques offer methods for detecting, and in some cases quantifying, the amount of viral nucleic acid in a sample. PCR is carried out using pairs of nucleic acids, termed "primers." Blotting procedures are carried out using nucleic acids termed "probes." Both probes and primers function through base-pairing with a target nucleic acid being detected. By way of example, nucleic acids complementary to SEQ ID NO: 1 and 3 constitute a primer pair. Similarly, exemplary nucleic acids complementary to either SEQ ID NO:1 and 3 (and fragments thereof) may be used as probes to detect SARS CoV spike glycoprotein. Primers and probes of the present invention may be any size greater than 6 nucleotides, but are preferably 8, 10, 12, 15, 20, 30 or 50 nucleotides in length, more preferably 100 or more nucleotides in length.

The term primer, as defined herein, is meant to encompass any nucleic acid that is capable of priming the synthesis of a nascent nucleic acid in a template-dependent process. Primers may be provided in double-stranded or single-stranded form, although the single-stranded form is preferred. Probes are defined differently, although they may act as primers. Probes, while perhaps capable of priming, are designed to bind to a target DNA or RNA and need not be used in an amplification process. In preferred embodiments, the probes and primers are labeled to aid in detection, as described below. Use of primers and probes in diagnostic and quantitative analytical procedures are well-known to those of skill in the art. For reference, several exemplary procedures representing preferred embodiments are described below.

a) Template Dependent Amplification Methods

A number of template dependent processes are available to amplify sequences present in a template sample. One of the best known amplification methods is PCR, which is described in detail in U.S. Pat. Nos. 4,683,195, 4,683,202 and 4,800,159. Briefly, in PCR, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

Reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. Polymerase chain reaction methodologies are well known in the art.

Another method for amplification is the ligase chain reaction ("LCR"). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Miller et al., PCT Application WO 89/06700 disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, M. A., In: PCR PROTOCOLS: A GUIDE TO METHODS AND APPLICATIONS, Academic Press, N.Y., 1990).

b) Southern/Northern Blotting

Blotting techniques are well known to those of skill in the art. Southern blotting uses DNA as a target, whereas Northern blotting uses RNA as a target. Each provides different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

IV. Peptides

Peptides of the present invention may provide a source of antigen suitable for use in vaccine preparations, and/or provide diagnostic reagents for the detection of SARS CoV infection.

A. Sources

1. Synthetic Peptides

Peptides of the present invention maybe synthesized by any of the techniques known to those skilled in the peptide art, including recombinant DNA techniques (see above), or may be isolated from natural sources, such as whole virus expressing proteins that include a segment having an amino acid sequence of the present invention.

Synthetic chemistry techniques, such as a solid-phase Merrifield-type synthesis, are preferred for reasons of purity, antigenic specificity, freedom from undesired side products, ease of production and the like. Excellent summaries of the many techniques available can be found in J. M. Steward & J. D. Young, SOLID PHASE PEPTIDE SYNTHESIS, W.H. Freeman Co., San Francisco, (1969); M. Bodanszky et al., PEPTIDE SYNTHESIS, John Wiley & Sons, Second Edition, (1976); and J. Meienhofer, HORMONAL PROTEINS AND PEPTIDES, Vol. 2, p. 46, Academic Press, New York (1983) for solid phase peptide synthesis, and E. Schroder & K. Kubke, 1 THE PEPTIDES, Academic Press, New York (1965) for classical solution synthesis, each being hereby incorporated herein by reference. Appropriate protective groups usable in such synthesis are described in the above texts and in J. F. W. McOmie, PROTECTIVE GROUPS IN ORGANIC CHEMISTRY, Plenum Press, New York (1973), the entire disclosure of which is also incorporated herein by reference. Simplified methods for solid phase synthesis of peptides on a small scale also are known. See for instance, Houghten, R. A., Proc. Natl. Acad. Sci. U.S.A. 82:5131-5135 (1985); and Houghton, M., Q.-L. Choo, & G. Kuo, European Patent Application 88310922 (1988).

2. Recombinant Peptides

Alternatively, recombinant DNA technology may be employed wherein a nucleotide sequence which encodes a protein comprising an antigenic immunogenic peptide of interest is inserted into an expression vector, transformed or transfected into an appropriate host cell and cultivated under conditions suitable for expression. These procedures are generally known in the art, as described generally in Sambrook et al., Molecular Cloning, A Laboratory Manual, Cold Spring Harbor Press, Cold Spring Harbor, N.Y. (1982), which is incorporated herein by reference.

Coding sequences for antigenic peptides and proteins of the present invention may be synthesized by chemical techniques, as described above. A number of vectors and suitable host systems are now available for expressing the coding sequence. Generally, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences known to those of skill in the art.

Standard techniques for construction of the expression cassettes and vectors suitable for expressing nucleic acids encoding peptides of the present invention are well known to those of ordinary skill in the art (Sambrook, J., Fritsch, E. F., and Maniatis, T., Molecular Cloning, A Laboratory Manual 2nd ed. (1989); Gelvin, S. B., Schilperoort, R. A., Varma, D. P. S., eds. Plant Molecular Biology Manual (1990)). A variety of strategies are available for ligating fragments of DNA, the choice depending on the nature of the termini of the DNA fragments.

In preparing the expression cassette, the various nucleic acid sequences may normally be inserted or substituted into a bacterial plasmid. Any convenient plasmid may be employed, which will be characterized by having a bacterial replication system, a marker which allows for selection in the bacterium and generally one or more unique, conveniently located restriction sites. These plasmids, referred to as vectors, may include such vectors as pACYC 184, pACYC 177, pBR322, pUC9, the particular plasmid being chosen based on the nature of the markers, the availability of convenient restriction sites, copy number, and the like. Thus, the sequence may be inserted into the vector at an appropriate restriction site(s), the resulting plasmid used to transform the E. coli host, the E. coli grown in an appropriate nutrient medium and the cells harvested and lysed and the plasmid recovered. One then defines a strategy that allows for the stepwise combination of the different fragments.

B. Fusion Molecules

Some embodiments the peptides may be synthetically conjugated to native fragments or particles, immunostimulatory molecules and the like to form advantageous fusion molecules. Both peptides and fusion molecules of the invention may be in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

One fusion molecule embodiment is a peptide or protein that includes in its amino acid sequence a sequence of at least 6 preferably more than 9, ideally more than 12, 15 or 16 contiguous amino acids present in SEQ ID NO:2 or 4.

Fusion molecules may be produced by methods known to those of skill in the art and are typically designed to improve antigenicity of the immunostimulatory peptide sequence included in the molecule, to aid in peptide delivery to a patient, or enhance the peptides utility as a diagnostic reagent.

In some aspects antigenically neutral carrier conjugates, e.g., proteins, provide improved characteristics by, for example, presenting the antigenic peptide potion of the fusion molecule in a favorable manner, or by increasing the effective serum half-life of the antigenic peptide.

Peptides may also be subject to various changes, such as substitutions, either conservative or nonconservative, where such changes might provide for certain advantages in their use. By conservative substitutions is meant replacing an amino acid residue with another that is biologically and/or chemically similar, e.g., one hydrophobic residue for another, or one polar residue for another. The substitutions include combinations such as Gly, Ala; Val, Ile, Leu, Met; Asp, Glu; Asn, Gln; Ser, Thr; Lys, Arg; and Phe, Tyr. The effect of single amino acid substitutions may also be probed using D-amino acids. Such modifications may be made using well known peptide synthesis procedures, as described in e.g., Merrifield, Science 232:341-347 (1986), Barany and Merrifield, The Peptides, Gross and Meienhofer, eds. (New York, Academic Press), pp. 1-284 (1979); and Stewart and Young, Solid Phase Peptide Synthesis, (Rockford, Ill., Pierce), 2d Ed. (1984).

The peptides of the invention may also be modified by extending their amino acid sequence, e.g., by the addition of amino acids to their N or C terminus. The peptides or fusion molecules of the invention can also be modified by altering the order or composition of certain residues, it being readily appreciated that the core amino acid sequence of at least 6 preferably more than 9, ideally more than 12, 15 or 16 contiguous amino acids present in SEQ ID NO:2 or 4 may generally not be appreciably altered without an adverse effect on biological activity. The noncritical amino acids need not be limited to those naturally occurring in proteins, such as L-α-amino acids, or their D-isomers, but may include non-natural amino acids as well, such as β-γ-δ-amino acids, as well as many derivatives of L-α-amino acids.

Fusion molecules may also comprise isosteres of two or more residues in the immunogenic peptide. An isostere as defined here is a sequence of two or more residues that can be substituted for a second sequence because the steric conformation of the first sequence fits a binding site specific for the second sequence. The term specifically includes peptide backbone modifications well known to those skilled in the art. Such modifications include modifications of the amide nitrogen, the α-carbon, amide carbonyl, complete replacement of the amide bond, extensions, deletions or backbone crosslinks. See, generally, Spatola, Chemistry and Biochemistry of Amino Acids, peptides and Proteins, Vol. VII (Weinstein ed., 1983).

Modifications of fusion molecules with various amino acid mimetics or unnatural amino acids are particularly useful in increasing the stability of the peptide in vivo. Stability can be assayed in a number of ways. For instance, peptidases and various biological media, such as human plasma and serum, have been used to test stability. See, e.g., Verhoef et al., Eur. J. Drug Metab Pharmacokin. 11:291-302 (1986). Half life of the peptides of the present invention is conveniently determined using a 25% human serum (v/v) assay. The protocol is generally as follows. Pooled human serum (Type AB, non-heat inactivated) is delipidated by centrifugation before use. The serum is then diluted to 25% with RPMI tissue culture media and used to test peptide stability. At predetermined time intervals a small amount of reaction solution is removed and added to either 6% aqueous trichloracetic acid or ethanol. The cloudy reaction sample is cooled (4° C.) for 15 minutes and then spun to pellet the precipitated serum proteins. The presence of the peptides is then determined by reversed-phase HPLC using stability-specific chromatography conditions.

Particularly preferred fusion proteins are linked together by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues.

Alternatively, the peptide may be linked in the fusion molecule without a spacer. Linkage may be at the amino or carboxy terminus of the peptide. The amino terminus of the peptide may be acylated. The carboxy terminus of the peptide may also be modified, e.g., by amidation, esterification or reduction of the carboxyl group. Methods for performing these modifications are well known to those of skill in the art.

C. Pharmaceutical Compositions

1. Formulating Pharmaceutical Compositions

Although the antigenic peptides of the invention may be used without conjugation to other molecules, the fusion molecule embodiments discussed above provide one useful pharmacological composition of the present invention. For example, lipids have been identified as agents capable of assisting the priming CTL in vivo against viral antigens. By way of example, palmitic acid residues can be attached to the alpha and epsilon amino groups of a Lys residue and then linked, e.g., via one or more linking residues such as Gly, Gly-Gly-, Ser, Ser-Ser, or the like, to an immunostimulatory peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunostimulatory peptide.

As another example of lipid priming of CTL responses, *E. coli* lipoproteins, such as tripalmitoyl-S-glycerylcysteinlyseryl-serine (P3 CSS) can be used to prime virus specific CTL when covalently attached to an appropriate peptide. See, Deres et al., Nature 342:561-564 (1989), incorporated herein by reference. Immunostimulatory peptides of the invention can be coupled to P3 CSS, for example, and the lipopeptide administered to an individual to specifically prime a CTL response to the target antigen. Further, as the induction of neutralizing antibodies can also be primed with P3 CSS conjugated to a peptide that displays an appropriate epitope, the two compositions can be combined to more effectively elicit both humoral and cell-mediated responses to infection.

Those skilled in the art of preparing pharmaceutical compositions will realize how to prepare the peptides and conjugates described above for pharmaceutical use in composition comprising accepted pharmaceutical carriers, particularly vaccines.

Peptides of the invention may also be bound to a carrier protein, according to methods known in the art. See, for instance, M. F. Good, Science 235:1059-1062 (1987); and Palker, T. J., J. 1 mm. 142:3612-3619 (1989). Agents which can be conjugated to peptides to provoke an immune response include toxoids such as diphtheria toxoid or tetanus toxoids, which are commonly recognized by the body (of immunized persons) and eliminated by the immune system. Alternatively, a nucleotide sequence encoding the peptide may be incorporated into a recombinant gene and expressed as part of a vector, for instance, a recombinant virus such as vaccinia virus made by the method of Chakrabarti, S., et al., Nature 320:535-537 (1986).

The peptide of the present invention also may be incorporated into a larger peptide comprising additional epitopes, either other T cell epitopes or B cell epitopes. Thus, for example, the peptide may be used as part of a multivalent vaccine that induces cytotoxic T cell responses to multiple epitopes of SARS CoV or of SARS CoV and another virus.

In addition, the multivalent vaccine peptide may include helper T cell epitopes and B cell epitopes of SARS CoV or another virus, to effect induction of an antibody response as well as a cytotoxic T cell response. For instance, one could attach a helper T cell epitope from HIV, such as those described in Cease K. B., et al., Proc. Natl. Acad. Sci. USA 84:4249-4253 (1987), to provide T cell help for the CTL response. For peptides generating antiviral cytotoxic T lymphocytes, Hart, M. K., et al., Proc Natl Acad Sci USA 88:9448-9452 (1991); and for peptides inducing an antibody response, Hart M., K., et al., J. Immunol. 145:2677-2685 (1990). Collett, N. S., V. Moennig, and M. C. Horzinek. 1989. Recent advances in pestivirus research. J. Gen. Virol. 70:253-266.

Generally, the invention provides a vaccine having an antigenic molecule having an antigenic amino acid sequence including at least 6 preferably more than 9, ideally more than 12, 15 or 16 contiguous amino acids present in SEQ ID NO:2 or 4, and a pharmaceutically acceptable excipient. Optional components may be added to the vaccine to further enhance its therapeutic effectiveness, shelf-life or other property desirable in a therapeutic composition. Optional components include adjuvants, buffers, emulsion material and the like.

2. Administering Antigenic Peptides

As with pharmaceutically-active nucleic acids, the antigenic peptides and fusion molecules of the invention are intended for parenteral, topical, oral, or local administration for prophylactic and/or therapeutic treatment. Preferably, the peptides of the present invention are administered intramuscularly, more preferably intranasally. Methods for delivering peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045.

In JP 309347/91 (priority Nov. 25, 1991) an orally or nasally administered immunogen composition comprising an immunogen capable of immunizing mammals using an adjuvant comprising of triglycerides with C6-26 residue of saturated or unsaturated fatty acid.

WO 94/17827 (priority Feb. 15, 1993) describes a pharmaceutical preparation for topical administration of antigens to mammals via mucosal membranes. The adjuvant/vehicle preparation is selected from (a) polyoxyethylene sorbitan monoesters, (b) polyoxyethylene castor oil, (c) caprylic/capric glycerides, and (d) gangliosides.

The peptides may be optionally administered to a patient dissolved in a pharmaceutically acceptable excipient, preferably an aqueous excipient. A variety of aqueous excipients may be used, e.g., water, buffered water, 0.4% saline, 0.3% glycine, and the like, including glycoproteins for enhanced stability, such as albumin, lipoprotein, globulin, etc. The compositions may also contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

Methods of achieving adjuvant effect for the vaccine include the use of agents such as aluminum hydroxide or phosphate (alum), commonly used as 0.05 to 0.1 percent solution in phosphate buffered saline or QS21 which stimulates cytotoxic T-cells. Formulations with different adjuvants that enhance cellular or local immunity can also be used. The relative proportion of adjuvant to antigenic peptide can be varied over a broad range so long as both are present in effective amounts. For example, aluminum hydroxide can be present in an amount of about 0.5% of the vaccine mixture ($Al_{12}O_3$ basis).

The concentration of the peptides of the present invention in pharmaceutical preparations can vary widely, i.e., from about 0.001% to as much as 15 or 20% by weight and will be selected primarily by fluid volumes, viscosities, etc., in accordance with the particular mode of administration selected. When utilized intramuscularly as an injection solution with the active ingredient in a therapeutically effective immunopotentiating amount of about 0.001 to 0.01% by weight. If prepared in the form of a tablet, capsule or suppository, it is preferred that the active ingredient be present in an amount of about 0.1 mg per tablet, suppository or capsule. In such form, the capsule, suppository or tablet may also contain other conventional excipients and vehicles such as fillers, starch, glucose, etc. Actual methods for preparing parenterally, orally, and topically administrable compounds will be known or apparent to those skilled in the art and are described in detail in, for example, Remington's Pharmaceutical Science, 17th ed., Mack Publishing Company, Easton, Pa. (1985), which in incorporated herein by reference.

Determination of an effective amount of antigenic peptide to treat individuals infected with SARS CoV may be performed using methods routine to those of skill in the art, and discussed in detail above for pharmaceutically active nucleic acids.

Compositions of the invention may be administered to an individual already suffering from an infection in an amount sufficient to cure or at least partially arrest the disease and its complications. An amount adequate to accomplish this is defined as "therapeutically effective dose." Amounts effective for this use will depend on the severity of the infection or disease and the weight and general state of the patient being treated, but generally range from about 0.001 mg/kg to about 5000 mg/kg host body weight of peptide per day, more commonly about 0.1 mg/kg to about 1000 mg/kg host body weight of peptide per day, usually about 0.25 mg/kg to about 100 mg/kg host body per day, more usually about 0.5 mg/kg to about 20 mg/kg host body weight per day, and preferably about 0.7 mg/kg to about 10 mg/kg host body weight per day. Maintenance dosages over a prolonged period of time may be adjusted as necessary. It must be kept in mind that the materials of the present invention may be employed in serious disease states, that is, life-threatening or potentially life threatening situations. In such cases, in view of the minimization of extraneous substances and general lack of immunogenicity when a human-derived polypeptide is employed to treat human hosts, it is possible and may be felt desirable by the treating physician to administer substantial excesses of these compositions.

In prophylactic applications, compositions containing the present invention are administered to a patient susceptible to or otherwise at risk for infection treated by the methods of the present invention. Such an amount is defined to be a "prophylactically effective dose." In this use, the precise amounts again depend on the patient's state of health and weight, but are generally in the ranges described above for therapeutic use. Prophylactic administration may be particularly desirable for hosts that have been exposed or at risk for exposure of infectious diseases, e.g., health-care workers, travelers, family members of infected individuals, immunosuppressed persons, and the like. The peptides of the present invention may also be administered for surgical prophylaxis to lessen the risk of infectious complications and enhance the host's restorative response to blood loss.

D. Diagnostic Applications for Peptides

Peptides of the present invention also find use as diagnostic reagents. For example, a peptide of the invention may be used to determine the susceptibility of a particular individual to a treatment regimen that employs the peptide or related peptides, and thus may be helpful in modifying an existing treatment protocol or in determining a prognosis for an affected individual. In addition, the peptides may also be used to predict which individuals will be at substantial risk for developing chronic infection.

An important aspect to the diagnosis and treatment of SARS-CoV is determination of the presence of viral infection, and when infection is present, monitoring the viral load or the infected individual. The present invention addresses these issues by providing methods of assessing immune function or diagnosing exposure to SARS CoV of an individual. Performing the methods involves contacting a blood sample from the individual that contains T cells with an antigenic peptide of the present invention; and, determining if peptide contact induces an immune response, preferably a CTL response. The blood sample will need to contain antigen-presenting cells. These cells may be endogenous to the sample, or added from an external source. Antigen-presenting cells can be normal cells such as peripheral blood mononuclear cells or dendritic cells (Inaba, et al., J. Exp. Med. 166:182 (1987); and Boog, Eur. J. Immunol. 18:219 [1988]).

Alternatively, the peptides may be used in an ELISA-type assay to detect anti-spike glycoprotein antibodies in an individual's blood. By way of example, immobilized peptides are contacted with a blood fraction containing antibodies from an individual suspected of being infected with the virus. After a suitable incubation time, the immobilized peptides are washed to remove material that is not specifically binding the peptides. Antibodies recognizing the immobilized peptides then may be detected using a second anti-IgG antibody. Preferably the second antibody is conjugated with a detectable label to facilitate identification. Alternative strategies for conducting ELISA-type assays using antigenic peptides are well known in the art.

V. Antibodies

Antibodies of the present invention find utility as agents for conferring passive immunity and in diagnostic applications for detection of SARS CoV in samples taken from infected cells or individuals.

Generally, antibodies of the present invention specifically bind a peptide comprising at least 6 contiguous amino acids from one of the peptides selected from SEQ ID NO:2 and 4. In the context of the present invention, the term "antibodies" includes single-chain antibodies, Fab and Fab2 fragments, and the like.

The following sections detail methods for producing antibodies suitable for the present invention, and their use. Antibodies produced using these methods may be tested for efficacy using the competitive and non-competitive assays.

A. Antibody Synthesis

Methods of producing polyclonal and monoclonal antibodies that react specifically with SARS spike glycoprotein or peptides thereof, particularly SEQ ID NO:2 or 4, are known to those of skill in the art (see, e.g., Coligan, Current Protocols in Immunology (1991); Harlow & Lane, supra; Goding, Monoclonal Antibodies: Principles and Practice (2d ed. 1986); and Kohler & Milstein, Nature 256:495-497 (1975). Such techniques include antibody preparation by selection of antibodies from libraries of recombinant antibodies in phage or similar vectors, as well as preparation of polyclonal and monoclonal antibodies by immunizing rabbits or mice with antigenic peptides of the present invention (see, e.g., Huse et al., Science 246:1275-1281 (1989); Ward et al., Nature 341:544-546 (1989)).

A number of antigenic peptides comprising SEQ ID NO: 2 and 4, or fragments thereof, may be used to produce antibodies specifically reactive with SARS CoV spike glycoprotein. For example, SEQ ID NO: 2 and 4 peptides, or fragments thereof, can be isolated as described herein. Recombinant protein can be expressed in eukaryotic cells as described above, and purified using methods known in the art. Alternatively, a synthetic peptide derived from the sequences disclosed herein and optionally conjugated to a carrier protein can be used as an antigenic peptide.

Methods for producing polyclonal antibodies are known to those of skill in the art. For example, an inbred strain of mice (e.g., BALB/C mice) or rabbits is immunized with the protein using a standard adjuvant, such as Freund's adjuvant, and a standard immunization protocol. Other suitable additives and/or adjuvants may be included where desired. Several additives useful in compositions of the present invention are provided below. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, Eur. J. Immunol. 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., Science 246:1275-1281 (1989).

Antigenic molecules of the invention can be detected and/or quantified using any of a number of well-recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-HIV envelope proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Once specific antibodies against SARS spike protein are available, SARS CoV may be detected by a variety of immunoassay methods. For a review of immunological and immunoassay procedures, see Basic and Clinical Immunology (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

B. Therapeutic Antibodies

Antibody compositions of the present invention may be used to confer short-term "passive immunity" to an infected individual or an individual suspected of being infected with the SARS CoV virus. This type of therapy is particularly useful for treating individuals suspected of being recently infected, as the endogenous immune response to the virus is generally too slow to prevent the infection becoming productive. By administering anti-SARS antibodies to a recently infected individual, the infection may be terminated, or at least slowed sufficient to allow the endogenous immune response to clear the infection. The procedure has also found use in treatment of individuals with immune systems compromised by age or disease.

Antibodies used therapeutically must not induce a immune response in the individual being treated. Thus antibodies useful for passive immune therapy must be harvested from a second individual of the same species as the treated individual, or must be genetically altered to remove antigenic determinants and expressed, for example as is the case for humanized murine antibodies. Methods for preparing and administering antibodies for passive immunity therapy are well known to those of skill in the art.

C. Diagnostics

Immunological binding assays (or immunoassays) typically use an antibody that specifically binds to a protein or antigen of choice (in this case epitopes of SEQ ID NO:2 or 4, or an antigenic subsequence thereof). For example one method for detecting the presence of SARS CoV in a sample involves contacting the sample with an antibody specifically recognizing a peptide comprising at least 6 contiguous amino acids from SEQ ID NO:2 or 4. Antibody binding to the peptide is then determined indicating the sample includes SARS CoV.

Immunoassays often use a labeling agent to specifically bind to and label the complex formed by antibody and antigen. The labeling agent may itself be one of the moieties comprising the antibody/antigen complex. Thus, the labeling agent may be a labeled polypeptide derived from SEQ ID NO:2 or 4, or a labeled anti-SARS spike glycoprotein antibody. Alternatively, the labeling agent may be a third moiety, such a secondary antibody, which specifically binds to the antibody/spike glycoprotein complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111: 1401-1406 (1973); Akerstrom et al., *J. Immu-* nol. 135:2589-2542 (1985)). The labeling agent can be modified with a detectable moiety, such as biotin, to which another molecule can specifically bind, such as streptavidin. A variety of detectable moieties are well known to those skilled in the art and discussed in greater detail below.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting recombinant SARS CoV in samples may be either competitive or noncompetitive. Non-competitive immunoassays are assays in which the amount of antigen is directly measured. In one preferred "sandwich" assay, for example, the anti-Spike glycoprotein antibodies are bound to a solid substrate on which they are immobilized. These immobilized antibodies then capture SARS CoV present in the test sample. The immobilized SARS CoV is then bound by a labeling agent, such as a second anti-spike glycoprotein antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety. A variety of labels suitable for use with the antibodies of the present invention are known and include those discussed in labeling diagnostic nucleic acids, above.

2. Competitive Assay Formats

In competitive assays, the amount of the SARS CoV present in the sample is measured indirectly by measuring the amount of known, added (exogenous) spike glycoprotein (or fragment thereof) displaced (competed away) from an anti-spike glycoprotein antibody by the unknown amount of SARS CoV present in the sample. In one competitive assay, a known amount of antigenic peptide from SEQ ID NO:2 or 4 (or a fragment thereof) is added to a sample and the sample is then contacted with an antibody that specifically binds to the spike glycoprotein. The amount of exogenous antigenic peptide bound to the antibody is inversely proportional to the concentration of SARS CoV present in the sample. In a particularly preferred embodiment, the antibody is immobilized on a solid substrate. The amount of antigenic peptide bound to the antibody may be determined either by measuring the amount of antigenic peptide present in a antibody/peptide complex, or alternatively by measuring the amount of remaining uncomplexed antigenic peptide. The amount of antigenic peptide may be detected by providing a labeled envelope fusion protein molecule.

A hapten inhibition assay is another preferred competitive assay. In this assay antigenic peptide from SEQ ID NO:2 or 4 (or a fragment thereof) is immobilized on a solid substrate. A known amount of anti-spike glycoprotein antibody is added to the sample, and the sample is then contacted with the immobilized antigenic peptide. The amount of anti-spike glycoprotein antibody bound to the known immobilized antigenic peptide is inversely proportional to the amount of SARS CoV present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody, as described above.

3. Western Blot Assays

The antibody compositions of the present invention also find use in immunoblot or Western blot analysis. The antibodies may be used as high-affinity primary reagents for the identification of spike glycoprotein protein immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

Detection of bound antibodies may be accomplished in any suitable fashion, including for example the use of labeled second antibody that specifically recognizes the anti-spike glycoprotein antibody, e.g., anti-IgG antibody. The second antibody may be labeled directly or indirectly. Suitable labels include chemiluminescent, fluorescent, or radionuclear compounds, microparticles, enzymes, or other labels known to be useful for detection.

Other assay formats include liposome immunoassays (LIA), which use liposomes designed to bind specific molecules (e.g., antibodies) and release encapsulated reagents or markers. The released chemicals are then detected according to standard techniques (see, Monroe et al., Amer. Clin. Prod. Rev. 5:34-41 (1986)).

VI. Kits

Kits including the nucleic acids or peptides discussed herein are another aspect of the present invention. Kit embodiments provide a convenient means for supplying those wishing to practice the invention with necessary reagents of the invention, ancillary reagents, apparatus, instruction and/or other components necessary to implement the invention. By way of example, one embodiment for the detection of SARS CoV in a sample provides, among other things, an isolated nucleic acid having at least 85% sequence homology to a second nucleic acid complementary to at least 15 contiguous nucleotides of SEQ ID NO:1 or 3, and specifically recognizing SEQ ID NO:1 or 3 under stringent conditions, and instructions for using the isolated nucleic acid to determine the presence of SARS CoV in the sample.

Another embodiment provides a pharmaceutical composition comprising an siRNA having at least 85% sequence homology to at least 15 contiguous nucleotides of SEQ ID NO:1 or 3, and inhibiting the viral production by 30%, as determined by reduction in viral titer, when tested with Vero monkey cells infected with the SARS CoV virus. This embodiment also contains instructions for the use of the pharmaceutical. A third embodiment comprises a peptide vaccine for the treatment or prevention of SARS CoV virus that includes an antigenic molecule having an antigenic amino acid sequence comprising at least 6 contiguous amino acids identical to at least 6 contiguous amino acids present in SEQ ID NO:2 or 4, and a pharmaceutically acceptable excipient.

The invention contemplates additional kits packaged to deliver, instruct and otherwise aid the practitioner in the use of the invention. These additional kits include those for the use of diagnostic embodiments of the invention, and their construction is well known by those of skill in the art provided with the regents claimed in the present invention.

All publications and patent applications cited in this specification are herein incorporated by reference as if each individual publication or patent application were specifically and individually indicated to be incorporated by reference.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results.

EXAMPLES

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results.

The SARS-CoV genome exhibits significant sequence variations amongst isolates. These genomic variations may aid the establishment of molecular epidemiological relationships between different isolates. These data demonstrate the rapid evolution of the SARS-CoV.

In this study, we aim to look for evidence of sequence variations in the virus genome. Complete and partial genomic sequences generated from eleven SARS patients with known epidemiological backgrounds were compared. Further comparisons were made with reference to other SARS-CoV sequences deposited at the National Center for Biotechnology Information (NCBI). This information is important for understanding the biology of this virus with implications for the therapeutic management and control of SARS.

Methods

SARS-related coronavirus in a clinical sample obtained from a patient in the Prince of Wales Hospital in Hong Kong was first cultured in Monkey Vero cell. Afterwards, the virus RNA genome was extracted and then reverse transcribe into cDNA. Then, an cDNA library was constructed. The insert in each cDNA clone was amplified by polymerase chain reaction (PCR). The genetic codes in the PCR products were determined by dideoxy sequencing followed by capillary electrophoresis in an automated sequencer. After searching the sequences generated against international nucleotide and protein databases, the identity of each sequence was assigned.

Viral RNA was extracted from Vero cell cultures established from specimens obtained from eleven SARS patients in Hong Kong. Viral genomic sequences were obtained by reverse transcription and dideoxy DNA sequencing. The sequences were compared with reference to the epidemiological background of the SARS cases.

Patients

The Prince of Wales Hospital, Hong Kong was the site of a major hospital outbreak of SARS. (Lee N, et al., N. Engl. J. Med. 2003 May 15;348(20):1986-94). Case definition was initially based on the clinical criteria established by the Centers for Disease Control and Prevention (CDC). Subsequent to the availability of evidence suggesting the association of a coronavirus with SARS suspected cases were subjected to virological assessments for the presence of the coronavirus. (Ksiazek T G, et al., N. Engl. J. Med. 2003 May 15; 348(20): 1953-66); Peiris J, et al., Lancet 2003; 361: 1319-25; Drosten C, et al., N. Engl. J. Med. 2003 May 15; 348(20):1967-76). Vero cell cultures with positive cytopathic effect were observed for 18 of the 58 tested samples. The presence of the SARS-CoV was confirmed by molecular studies. Genetic analysis performed on the viral RNA extracted from 11 of the 18 positive cases formed the subject of this investigation. Ten of these samples were cultured from nasopharyngeal aspirates and the remaining one was cultured from a small bowel biopsy obtained at autopsy. All eleven patients had serological evidence of SARS-coronavirus infection.

RNA Extraction

RNA was extracted from 2.24 ml or 280 µl (for whole genome sequencing or spike glycoprotein gene sequencing, respectively) of viral culture supernatant by the use of a QIAamp Viral RNA Mini Kit (Qiagen), according to the manufacturer's instructions. An elution volume of 60 µl was used.

Genome Sequencing

To facilitate the sequencing of the virus genome, several genomic libraries were constructed. Briefly, reverse transcription was carried out using the Superscript III reverse transcriptase (Invitrogen) and primed by either random hexamers (Applied Biosystems) or primers designed to amplify conserved regions of known coronaviruses. The products were then TA-cloned into a plasmid vector (pGEM-T Easy Vector System, Promega). Following the release of the draft sequence of the Tor2 strain of the SARS CoV by the Genome Sciences Center, Canada (GenBank accession number AY274119), PCR primers were designed to amplify multiple overlapping fragments of the SARS-CoV genome (online supplement). DNA sequencing was performed by the dideoxy dye terminator method, using automated DNA sequencers based on capillary electrophoresis. The complete sequences of two viral isolates (to be described in Results) were analyzed (deposited in GenBank, accession numbers AY278554 and AY282752). These two genomic sequences were compared with other SARS-CoV sequences available at GenBank. Apart from the full genome sequencing of the two viral isolates, the putative spike glycoprotein gene of the SARS-CoV was sequenced for the isolates from 9 other patients. Sequences were edited, aligned and comparisons were made using the CLUSTAL X software. Regions that reveal nucleotide substitutions were confirmed by re-sequencing with six- to eight-fold redundancy, using a combination of different primer sets, to ensure the quality of the sequencing data.

Results

Complete Genome Sequencing of a Viral Isolate Associated with a Major Hospital Outbreak Complete genome sequencing was performed for two viral isolates obtained from patients with distinct epidemiological backgrounds. Significant sequence variations were observed. One isolate (CUHK-Su-10) was epidemiologically linked to the first cluster of SARS cases originating from a Hong Kong hotel. The other isolate (CUHK-W1) was obtained from a patient with a recent travel history to southern China, and the sequence was almost identical to the isolates reported from Beijing and Guangzhou, China. The viral spike glycoprotein gene was sequenced for an additional nine patients. Six of these were epidemiologically linked to the CUHK-Su-10 isolate; with the spike glycoprotein gene being identical amongst these seven cases. The remaining three subjects, as in the case of CUHK-W1, were epidemiologically distinct from the CUHK-Su-10 isolate. CUHK-W1 and two of these remaining cases exhibited unique sequence variations in the spike glycoprotein gene.

The index patient ("J") at our hospital was a 26-year-old ethnic Chinese man who was admitted to the Prince of Wales Hospital on Mar. 4, 2003 was epidemiologically linked to the first local case of SARS, a nephrologist from Zhongshan, Guangdong Province, China, (FIG. 2) who visited Hong Kong in late February 2003. (Ksiazek T G, et al. N. Engl. J. Med. 2003 May 15;348(20):1953-66). Four days prior to symptom onset, J visited the hotel at the same floor where the nephrologist stayed. Patient 1 was J's mother who lived with J (FIG. 1) and previously enjoyed good health. She started to have fever, chills and rigors since Mar. 6, 2003. She developed non-productive cough, myalgia and nausea, but no vomiting or diarrhea. Her condition deteriorated with progressive shortness of breath. Seven days later, she was admitted to the Prince of Wales Hospital in critical condition, with a temperature of 39.7° C. and an oxygen saturation of 77% in room air. Chest X-ray showed bilateral patchy consolidation. She required 100% oxygen to maintain a saturation of 94%. She was transferred to the Intensive Care Unit nine hours later. Despite aggressive treatment, she succumbed one month later. A nasopharyngeal aspirate was obtained from her on admission and SARS-CoV was cultured from this sample (viral isolate CUHK-Su-10).

We obtained sequence for 29736 nucleotides (GenBank accession number AY282752). Ten open reading frames (ORFs) were predicted. A schematic diagram illustrating the location of these ORFs is shown in FIG. 4. The arrangement of the ORFs is consistent with the general organization of coronaviruses, in particular, the order of the predicted ORFs for the genes encoding the orf 1 ab polyprotein (including the polymerase protein), spike glycoprotein, envelope protein, membrane protein and nucleocapsid protein is as described for coronaviruses. (Lai M M C and Holmes K V. Coronaviridae: The viruses and their replication. In: Fields B N, Howley P M, Griffin D E, et al., eds. Fields Virology. 4th ed. Philadelphia: Lippincott Williams and Wilkins, 2001: 1163-85). On the amino acid level, sequence homologies (using translated BLAST) were observed for ORFs 1a, 1b, spike glycoprotein, membrane protein and nucleocapsid protein to segments of the corresponding proteins for murine hepatitis virus and bovine coronavirus. The levels of homology ranged from 51% to 76%. No significant homology was observed for the envelope protein to known coronaviruses.

Complete Genome Sequencing of a Second Viral Isolate

To investigate the possibility that different strains of SARS-CoV might exist, we sequenced the entire genome of an additional viral isolate. To maximize the probability of identifying a different strain, sequencing was performed on a specimen obtained from a patient who was not epidemiologically traceable to J. Consequently, the CUHK-W1 isolate was obtained from the Vero cell culture supernatant established from the nasopharyngeal aspirate from patient 8 (FIG. 1). Patient 8 had a history of traveling to Shenzhen, Guangdong Province, China (FIG. 2), 5 days before the onset of his symptoms. He was in Thailand when his symptoms occurred. He complained of fever, chills, myalgia and repeated vomiting. His chest X-ray showed haziness in the right hilar and left middle zones. On admission, he had a temperature of 38.5° C., with a lymphocyte count of 3.9×109/L (4-10.8×109/L). He had no contact with J prior to the onset of symptoms. The sequence of this virus isolate was deposited in the GenBank (accession number AY278554). Once again the sequence corresponds to that of a novel coronavirus.

Comparison of Genome Sequences of Viral Isolates

Ten nucleotide differences were observed between the viral isolates from Patient 1 and Patient 8 (Table 1). Seven of these resulted in amino acid substitutions, involving the orf1ab polyprotein, spike glycoprotein, membrane protein and nucleocapsid protein. The availability of other SARS-CoV sequences in GenBank has allowed us to make comparison between the sequences of our viral isolates to those sequenced by other groups (Table 1). Five nucleotide differences were observed between the viral isolate from Patient 1 (CUHK-Su-10) and the Tor2 sequence, resulting in four amino acid substitutions, involving the spike glycoprotein, membrane protein, nucleocapsid protein and a putative ORF (ORF 3 in FIG. 4). Eight nucleotide differences were observed between the CUHK-Su-10 isolate and the CDC-Urbani sequence (GenBank accession number AY278741), resulting in four amino acid substitutions, involving the orf 1 ab polyprotein, membrane protein and nucleocapsid protein. The CUHK-Su-10 isolate had two nucleotides which were unique amongst these 4 complete genomic sequences (positions 26477 and 28696).

The viral isolate from Patient 8 (CUHK-W1) exhibited 11 and 12 nucleotide differences from the Tor2 and CDC-Urbani sequences, respectively, both resulting in seven amino acid substitutions. It is of particular interest to note that the CUHK-W1 isolate had a number of unique nucleotide sequences when compared with the CUHK-Su-10, Tor2 and CDC-Urbani sequences, namely, at positions 7746, 9404, 9479, 17564, 21721, 22222 and 27827. The recent availability of the partial genomic sequences from a number of viral isolates from mainland China (Institute of Microbiology and Epidemiology, Academy of Military Medical Sciences/Beijing Genomics Institute, Chinese Academy of Sciences, GenBank accession numbers AY278489, AY278488, AY278487 and AY278490) has allowed us to compare these sequences with that of CUHK-W1. This comparison indicates the striking observation that at 5 out of these 7 positions, the CUHK-W1 isolate shows identity with the Chinese isolates (Table 1). Indeed, for the isolate from Guangzhou (GZ01), 6 of these 7 positions were identical with those for CUHK-W1. These results were especially relevant in view of the travel history of Patient 8 (FIG. 1) and the close proximity between Guangzhou and Shenzhen (FIG. 2).

Sequence Comparison for the Spike Glycoprotein Gene

The observation of sequence variations of different SARS-CoV isolates prompted us to undertake sequencing of additional isolates. We chose to sequence the spike glycoprotein gene for an additional 9 patients. Epidemiological information for these 9 patients is illustrated in FIG. 1. Patients 2, 3, 4, 5, 6, and 7 could all be epidemiologically traced back to J as the source of infection with symptom onset well clustered in time. These cases were thus classified as victims of the secondary infection cohort (FIG. 5A).

Patients 9, 10 and 11, on the other hand, represented an epidemiologically distinct cohort, either temporally and/or spatially (FIG. 5A). Patient 9 worked temporarily at the Prince of Wales Hospital where he assisted in the transport of patients between wards. He had never contacted J. He first noted myalgia on Mar. 25, 2003, some 2 weeks after the onset date of the patients in the secondary infection cohort (for example, the last one being Patient 6 whose date of onset was Mar. 11, 2003). Patients 10 and 11 acquired their infection from another hospital (Hospital B) with no prior admission to the Prince of Wales Hospital.

Sequence analysis of the spike glycoprotein gene revealed that the viral isolates from Patients 2, 3, 4, 5, 6 and 7 all had the same sequence as Patient 1 (FIG. 5B). The viral isolates from Patients 9 and 10, on the other hand, each had a single nucleotide change from the sequence of Patient 1. Furthermore, these nucleotide changes resulted in amino acid substitutions, threonine to isoleucine for Patient 9 and alanine to valine for Patient 10. The spike glycoprotein gene for the viral isolate from Patient 11 was identical to that of Patient 1.

Discussion

In this study we have obtained the complete nucleotide sequences of two SARS-CoV isolates investigated in our center. One of the isolates (CUHK-Su-10) was directly associated with the major hospital outbreak that we have previously reported.1 Our index case (J) was in turn epidemiologically linked to the index case in a Hong Kong hotel, 2, 3, 7 the nephrologist who previously worked in Zhongshan, China (FIG. 2). (Tsang K W, et al. N. Engl. J. Med. 2003 May 15;348(20):1977-85). The second isolate was derived from an individual who had a recent travel history to Shenzhen, China. The sequences from these epidemiologically distinct viral isolates revealed a number of nucleotide differences, including those that would result in amino acid substitutions. The availability of either complete or partial viral sequences from other groups has allowed us to make further observations on our sequence data. Thus, amongst the four complete viral sequences, CUHK-Su-10, CUHK-W1, Tor2 and CDC-Urbani, CUHK-Su-10 and Tor2 show the closest similarity with one another, with only five nucleotide differences (Table 1). The most likely explanation for this observation is the fact that both CUHK-Su-10 and Tor2 were linked epidemiologically to the hotel stay of the Chinese nephrologist (FIG. 2B). (Tsang K W, et al. N. Engl. J. Med. 2003 May 15;348(20):1977-85). Amongst the four complete viral sequences discussed in this paper, CUHK-W1 exhibited the greatest number of differences from the other three. However, a comparison of CUHK-W1 with the partial sequences for four viral isolates from mainland China revealed a much closer relationship. This observation is consistent with the history of Patient 8, which suggests that he had probably acquired his infection from Shenzhen, China. Among the sequences from mainland China, three viral isolates originated from patients in Beijing, while the remaining one was obtained from a patient in Guangzhou, China. Geographically, Zhongshan, Shenzhen and Guangzhou are cities in the Guangdong Province of China (FIG. 2). Zhongshan is located 200 km from the latter two cities, while Guangzhou is 160 km from Shenzhen. Hong Kong is located adjacent to Shenzhen, with the two cities sharing one border. The facts highlighted in the previous two paragraphs suggest that since the emergence of SARS-CoV in southern China, the virus has developed into at least two strains. One of the strains was closely related to the CUHK-Su-10 isolate, traceable to the nephrologist from Zhongshan, China (FIG. 3). (Tsang K W, et al. N. Engl. J. Med. 2003 May 15;348(20):1977-85). The second strain, on the other hand, was closely related to CUHK-W1, which in turn was similar to viral isolates partially sequenced from Guangzhou and Beijing (FIG. 3). This fact is particularly alarming as the first reports of SARS only began in November 2002 in Guangdong Province. (Update: outbreak of severe acute respiratory syndrome-Worldwide, 2003 MMWR Morb Mort Wkly Rep 2003;52:241-8). Thus, the presently observed viral evolution has taken place just in a matter of months. Further sequencing efforts would be expected to reveal yet more strains of the virus. This realization of viral evolution prompted us to carry out sequence analysis of additional viral isolates. We chose to sequence the spike glycoprotein gene because of the numerous roles that this glycoprotein plays in the biology and pathogenesis of coronavirus infections. (Lai M M C and Holmes K V. Coronaviridae: The viruses and their replication. In: Fields B N, Howley P M, Griffin D E, et al., eds. Fields Virology. 4th ed. Philadelphia: Lippincott Williams and Wilkins, 2001:1163-85). The spike glycoprotein forms the prominent, petal-shaped spikes on the surface of the virion. This glycoprotein plays a central role in the binding of the virion to specific receptors on the surface of susceptible cells. Importantly, mutations of the spike glycoprotein gene have been associated with changes in the tropism and pathogenicity of the virus. (Ballesteros M L, et al., Virology 1997;227:378-88; Wang F I, et al., Virology 1992; 186:742-9). Our data indicate that within the well-defined secondary infection cohort (Patients 1, 2, 3, 4, 5, 6 and 7), the sequence of the spike glycoprotein gene was identical in all of the studied isolates (FIG. 5B). On the contrary, sequence variations in the spike gene were readily observed for isolates which were epidemiologically distinct either temporally and/or spatially (Patients 8, 9 and 10). It is particularly important to note that amino acid substitutions were expected for the sequence variations for all of the latter three cases. The case of Patient 9 was particularly interesting as this subject had acquired SARS as a tertiary case. In other words, this sequence variation probably represented the continual evolution of the virus during the period from the secondary to the tertiary cases. Our study thus highlights the rapid evolution in the SARS-CoV genome. Such a phenomenon might be the consequence of the relatively high error frequencies of viral RNA polymerases in general. (Steinhauer D A and Holland J J. J Virol 1986;57:219-28.; Steinhauer D A, et al., Gene 1992;122:281-8). Furthermore, it is apparent from our analysis that the sequence variations in the SARS-CoV genome may show correlation with the geographical origin of the virus strain (FIG. 3). This correlation is demonstrable in the virus strains isolated within a city and between cities. Thus, molecular analysis may be a useful additional tool for the conduct of epidemiological investigations of SARS. For instance, such a line of investigation might ultimately allow one to identify the presumed animal ancestor of the SARS-CoV. An equally important line of investigation would be the study of the possible effects of these sequence variations on the infectivity, tissue tropism and pathogenicity of the virus. Diagnostically, it would be prudent to develop diagnostic assays to detect the less variable regions of the viral genome. In the longer term, it is hoped that a detailed understanding of the biology of this virus would allow us to develop new therapeutic and vaccination approaches against SARS.

TABLE 1

Comparison of genetic sequences of eight isolates of the SARS-CoV

| Nucleotide position[a] | CDC Urbani[b] AY278741 | BCCA Tor2[b] AY274119 | CUHK W1[b] AY278554 "Patient 8" | CUHK Su-10[b] AY282752 "Patient 1" | IME/BGI GZ01[c] AY278489 | IME/BGI BJ01[c] AY278488 | IME/BGI BJ02[c] AY278487 | IME/BGI BJ03[c] AY278490 |
|---|---|---|---|---|---|---|---|---|
| orf1ab polyprotein | | | | | | | | |
| 7746 | G Proline | G Proline | T Proline | G Proline | G | G | G | G |
| 7919 | T Valine | C Alanine | C Alanine | C Alanine | C | C | C | C |
| 9404 | T Valine | T Valine | C Alanine | T Valine | C | C | C | C |
| 9479 | T Valine | T Valine | C Alanine | T Valine | C | T | T | T |
| 16622 | T Alanine | C Alanine | C Alanine | C Alanine | C | C | C | C |
| 17564 | T Aspartate | T Aspartate | G Glutamate | T Aspartate | G | G | G | G |
| 17846 | C Arginine | C Arginine | T Arginine | T Arginine | C | C | C | C |
| 19064 | G Glutamate | A Glutamate | G Glutamate | A Glutamate | A | A | A | A |
| Spike glycoprotein | | | | | | | | |
| 21721 | G Glycine | G Glycine | A Aspartate | G Glycine | — | — | A | — |
| 22222 | T Isoleucine | T Isoleucine | C Threonine | T Isoleucine | C | C | C | C |
| 23220 | T Serine | G Alanine | T Serine | T Serine | T | T | T | T |
| 24872 | C Leucine | T Leucine | T Leucine | T Leucine | T | T | — | T |
| Unknown protein | | | | | | | | |
| 25298 | G Glycine | A Arginine | G Glycine | G Glycine | G | G | G | G |
| M protein | | | | | | | | |
| 26477 | T Phenyl-alanine | T Phenyl-alanine | T Phenyl-alanine | G Cysteine | T | T | T | T |
| 26857 | C Proline | T Serine | T Serine | T Serine | T | T | T | — |
| Non-orf | | | | | | | | |
| 27827 | T | T | C | T | — | C | C | C |
| Nucleocapsid protein | | | | | | | | |
| 28696 | G Glycine | G Glycine | G Glycine | T Cysteine | G | G | G | G |

Isolates are named according to the sequencing center, strain and GenBank accession number.
[a]Nucleotide numbering is based on the CDC-Urbani isolate (GenBank accession number AY278741).
[b]Isolates with sequence information on the complete genome. The complete genomic sequences were compared and a total of 17 nucleotide substitutions were identified among these isolates. Amino acid of the corresponding codon is indicated below the nucleotide information for each of the vital isolate with complete genomic information.
[c]Isolates with partial genomic sequences. Sequence comparison is limited to the 17 sites of nucleotide substitution identified from the complete genomes[b]. Nucleotide positions lacking sequence information is denoted by "—".

What is claimed is:

1. A method for detecting SARS CoV in a sample comprising contacting the sample with a diagnostic nucleic acid having a nucleotide sequence having at least 85% sequence identity to at least 15 contiguous nucleotides complementary to SEQ ID NO:1 or 3, and hybridizing to SEQ ID NO:1 or 3 under stringent conditions.

2. The method according to claim 1, wherein the sample is a nasal discharge, stool sample, or blood sample.

3. The method according to claim 1, further comprising PCR amplification of the target nucleic acid wherein the diagnostic nucleic acid is a primer and detecting the target nucleic acid.

4. The method according to claim 1, wherein the diagnostic nucleic acid comprises a label.

* * * * *

SEQUENCE LISTING

<160> NUMBER OF SEQ ID NOS: 4

<210> SEQ ID NO 1
<211> LENGTH: 549
<212> TYPE: DNA
<213> ORGANISM: severe acute respiratory syndrome (SARS) virus
<220> FEATURE:
<223> OTHER INFORMATION: DNA encoding severe acute respiratory syndrome
    (SARS) coronavirus (SARS CoV) C-terminal spike
    protein peptide

<400> SEQUENCE: 1

```
aactgtgttg ttaatgatgc caataacgac atcacaattt cctgagacaa atgtattgtc    60
tgtagtaatt atttgtggag aaaagaagtt cctctgtgta ataaaccaag aagtgccatt   120
aaacacaaaa acaccttcac gagggaagta tgctttgcct tcatgacaaa ttgctggcgc   180
tgtggtgaaa ttcctctcct gggatggcac atacgtgaca tgtaggaaga caacaccatg   240
cggggctgct tgtgggaagg acataaggtg gtagcccttt ccacaaaagt caactctttt   300
tgattgtcca agaacacact cagacatttt agtagcagca agattagcag aagccctgat   360
ttcagcagcc ctgattagtt gttgtgttac ataggtttga aggctttgaa gtctgcctgt   420
aattaacctg tcaatttgta cctccgcctc gactttatca agtcgcgaaa ggatatcatt   480
tagcacactt gaaattgcac caaaattaga gctaagttgt taacaagtg tgtttaatgc    540
ttgagcatt                                                           549
```

<210> SEQ ID NO 2
<211> LENGTH: 183
<212> TYPE: PRT
<213> ORGANISM: severe acute respiratory syndrome (SARS) virus
<220> FEATURE:
<223> OTHER INFORMATION: severe acute respiratory syndrome (SARS)
    coronavirus (SARS CoV) C-terminal spike protein
    peptide, sequence 1

<400> SEQUENCE: 2

```
Asn Ala Gln Ala Leu Asn Thr Leu Val Lys Gln Leu Ser Ser Asn Phe
  1               5                  10                  15

Gly Ala Ile Ser Ser Val Leu Asn Asp Ile Leu Ser Arg Leu Asp Lys
                 20                  25                  30

Val Glu Ala Glu Val Gln Ile Asp Arg Leu Ile Thr Gly Arg Leu Gln
             35                  40                  45

Ser Leu Gln Thr Tyr Val Thr Gln Gln Leu Ile Arg Ala Ala Glu Ile
         50                  55                  60

Arg Ala Ser Ala Asn Leu Ala Ala Thr Lys Met Ser Glu Cys Val Leu
 65                  70                  75                  80

Gly Gln Ser Lys Arg Val Asp Phe Cys Gly Lys Gly Tyr His Leu Met
                 85                  90                  95

Ser Phe Pro Gln Ala Ala Pro His Gly Val Val Phe Leu His Val Thr
            100                 105                 110

Tyr Val Pro Ser Gln Glu Arg Asn Phe Thr Thr Ala Pro Ala Ile Cys
        115                 120                 125

His Glu Gly Lys Ala Tyr Phe Pro Arg Glu Gly Val Phe Val Phe Asn
    130                 135                 140

Gly Thr Ser Trp Phe Ile Thr Gln Arg Asn Phe Phe Ser Pro Gln Ile
145                 150                 155                 160

Ile Thr Thr Asp Asn Thr Phe Val Ser Gly Asn Cys Asp Val Val Ile
                165                 170                 175

Gly Ile Ile Asn Asn Thr Val
            180
```

<210> SEQ ID NO 3
<211> LENGTH: 423
<212> TYPE: DNA

```
<213> ORGANISM: severe acute respiratory syndrome (SARS) virus
<220> FEATURE:
<223> OTHER INFORMATION: DNA encoding severe acute respiratory syndrome
      (SARS) coronavirus (SARS CoV) N-terminal spike
      protein peptide

<400> SEQUENCE: 3
cccatgggta cacagacaca tactatgata ttcgataatg catttaattg cactttcgag      60
tacatatctg atgccttttc gcttgatgtt tcagaaaagt caggtaattt taaacactta     120
cgagagtttg tgtttaaaaa taaagatggg tttctctatg tttataaggg ctatcaacct     180
atagatgtag ttcgtgatct accttctggt tttaacactt tgaaacctat ttttaagttg     240
cctcttggta ttaacattac aaatttaga gccattctta cagccttttc acctgctcaa      300
gacacttggg gcacgtcagc tgcagcctat tttgttggct atttaaagcc aactacattt     360
atgctcaagt atgatgaaaa tggtacaatc acagatgctg ttgattgttc tcaaaatcca     420
ctt                                                                   423

<210> SEQ ID NO 4
<211> LENGTH: 141
<212> TYPE: PRT
<213> ORGANISM: severe acute respiratory syndrome (SARS) virus
<220> FEATURE:
<223> OTHER INFORMATION: severe acute respiratory syndrome (SARS)
      coronavirus (SARS CoV) N-terminal spike protein
      peptide, sequence 2

<400> SEQUENCE: 4

Pro Met Gly Thr Gln Thr His Thr Met Ile Phe Asp Asn Ala Phe Asn
 1               5                  10                  15

Cys Thr Phe Glu Tyr Ile Ser Asp Ala Phe Ser Leu Asp Val Ser Glu
            20                  25                  30

Lys Ser Gly Asn Phe Lys His Leu Arg Glu Phe Val Phe Lys Asn Lys
        35                  40                  45

Asp Gly Phe Leu Tyr Val Tyr Lys Gly Tyr Gln Pro Ile Asp Val Val
    50                  55                  60

Arg Asp Leu Pro Ser Gly Phe Asn Thr Leu Lys Pro Ile Phe Lys Leu
65                  70                  75                  80

Pro Leu Gly Ile Asn Ile Thr Asn Phe Arg Ala Ile Leu Thr Ala Phe
                85                  90                  95

Ser Pro Ala Gln Asp Thr Trp Gly Thr Ser Ala Ala Ala Tyr Phe Val
            100                 105                 110

Gly Tyr Leu Lys Pro Thr Thr Phe Met Leu Lys Tyr Asp Glu Asn Gly
        115                 120                 125

Thr Ile Thr Asp Ala Val Asp Cys Ser Gln Asn Pro Leu
    130                 135                 140
```